(12) United States Patent
Hubbard

(10) Patent No.: US 10,492,545 B2
(45) Date of Patent: *Dec. 3, 2019

(54) CHEST WALL ADAPTER DEVICE

(71) Applicant: HUBBARD INNOVATIONS, INC., Virginia Beach, VA (US)

(72) Inventor: Thomas J. Hubbard, Virginia Beach, VA (US)

(73) Assignee: Hubbard Innovations, Inc., Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,787

(22) Filed: May 10, 2019

(65) Prior Publication Data

US 2019/0261700 A1  Aug. 29, 2019

Related U.S. Application Data

(63) Continuation-in-part of application No. 16/049,984, filed on Jul. 31, 2018, now Pat. No. 10,334,892.

(60) Provisional application No. 62/586,913, filed on Nov. 16, 2017, provisional application No. 62/754,845, filed on Nov. 2, 2018.

(51) Int. Cl.
*A41C 3/12* (2006.01)
*A41C 3/00* (2006.01)
*A41C 3/06* (2006.01)
*A61F 2/12* (2006.01)

(52) U.S. Cl.
CPC ............ *A41C 3/122* (2013.01); *A41C 3/0064* (2013.01); *A41C 3/06* (2013.01); *A61F 2/12* (2013.01)

(58) Field of Classification Search
CPC .............................. A41C 3/122; A41C 3/0064
USPC ........................................ 450/80, 41, 45–53
See application file for complete search history.

(56) References Cited

U.S. PATENT DOCUMENTS

| | | | |
|---|---|---|---|
| 3,077,196 A | 2/1963 | Paxton | |
| 3,446,213 A * | 5/1969 | Goldman | A41C 3/10 450/39 |
| 3,503,404 A * | 3/1970 | Evers | A41C 3/06 450/39 |
| 5,037,348 A | 8/1991 | Farino | |

(Continued)

FOREIGN PATENT DOCUMENTS

| | | |
|---|---|---|
| CN | 1928923 A | 3/2007 |
| CN | 100442314 C | 12/2008 |

(Continued)

*Primary Examiner* — Gloria M Hale
(74) *Attorney, Agent, or Firm* — Drinker Biddle & Reath LLP

(57) ABSTRACT

A chest wall adapter apparatus for supporting a user's breasts includes a right section and a left section, wherein the right section and the left section are contiguous on a front side of the apparatus. The apparatus also includes an inwardly extending convex portion located between the right section and the left section, wherein the inwardly extending convex portion is configured to lie against the chest wall of the user between the breasts; a horizontally extending and upwardly angled right shelf configured to extend along the right section and follow a contour along an underside of a right breast of the user; and a horizontally extending and upwardly angled left shelf configured to extend along the left section and follow a contour along an underside of the left breast of the user.

20 Claims, 20 Drawing Sheets

(56) References Cited

U.S. PATENT DOCUMENTS

| | | | |
|---|---|---|---|
| 5,716,255 A * | 2/1998 | Abercrombie | A41C 3/12 2/267 |
| 6,447,365 B1 | 9/2002 | Powell et al. | |
| 6,953,380 B2 * | 10/2005 | Brothers | A41C 3/0007 450/41 |
| 7,077,719 B2 | 7/2006 | Shiekman | |
| 7,234,994 B2 * | 6/2007 | Fildan | A41C 3/128 450/41 |
| RE40,487 E | 9/2008 | Eaton | |
| 7,666,058 B2 | 2/2010 | Smith | |
| 7,909,675 B1 | 3/2011 | Rainey | |
| 9,681,691 B1 | 6/2017 | Hubbs | |
| 9,681,692 B2 | 6/2017 | Hansen | |
| 2002/0102913 A1 | 8/2002 | Courtney et al. | |
| 2016/0183617 A1 | 6/2016 | McKinney | |
| 2016/0302492 A1 | 10/2016 | Sobah | |
| 2017/0006927 A1 | 1/2017 | Horndeski | |
| 2017/0127732 A1 | 5/2017 | Trangmar et al. | |
| 2017/0135427 A1 | 5/2017 | Yeung | |
| 2017/0151770 A1 | 6/2017 | Bauer | |
| 2017/0281367 A1 | 10/2017 | Ketchum et al. | |
| 2019/0142080 A1 * | 5/2019 | Hubbard | A41C 3/122 |

FOREIGN PATENT DOCUMENTS

| | | |
|---|---|---|
| CN | 205512406 U | 8/2016 |
| JP | 2015-054089 A | 3/2015 |
| JP | 2016-214829 A | 12/2016 |
| WO | 99/25536 A1 | 5/1999 |
| WO | 2014/131924 A1 | 9/2014 |
| WO | 2016/090093 A1 | 6/2016 |
| WO | 2017/143312 A1 | 8/2017 |

* cited by examiner

CHEST WALL ADAPTER DEVICE

CROSS-REFERENCE TO RELATED APPLICATIONS

This application is a continuation-in-part of U.S. application Ser. No. 16/049,984, filed Jul. 31, 2018, which claims the priority benefit of U.S. Provisional Application No. 62/586,913, filed Nov. 16, 2017. This application claims the priority benefit of U.S. Provisional Application No. 62/754,845, filed Nov. 2, 2018. Each of the above-cited documents is incorporated herein by reference in its entirety.

TECHNICAL FIELD

The present disclosure relates generally to support apparatuses, and more particularly to a chest wall adapter device.

BACKGROUND

Historically, it was thought that shoulder straps were the key to lifting and supporting breasts. Then European bra makers carried the underwire to another level—designing a much more substantial back strap that more efficiently transmitted pressure to better a designed underwire. By tightening the back strap, the back strap provided greater support without the discomfort of tight shoulder straps. Bra makers also realized that it was more efficient to support breasts from below rather than pulling them up with shoulder straps (this same advancement occurred in backcountry backpacks, which are now supported mostly by a waist strap rather than uncomfortable shoulder straps).

More recently, advances in bra technology have plateaued because of the anatomic variations between the chest walls of different users. Mass-produced underwires cannot hug many irregular ribs and breast bones, which results in loss or lack of support and/or discomfort for many users. This is one reason why a number of users simply cannot find a properly fitting bra.

Breast implants are not the same as the breast. Breast implants are not in the breast but behind it. But it turns out both breasts and breast implants are most powerfully manipulated in position by firmly opposed to the skin well-fitting underwires. The analogy stops there though because implant manipulation does not need the cup of the bra, and consequences to implant position can be long term even after stopping the underwire use. This is especially true in the seven or so months following breast implant surgery. Existing post-operative breast implant position manipulation solutions suffer from many of the same deficiencies as existing bra technology. Primary among them are infinite chest wall shapes that must be hugged/opposed by mass-produced underwires.

Examples of common body shapes that are not supported by existing bra designs and post-operative implant manipulation solutions include: (1) a caved in central chest (pectus excavatum); (2) an overly prominent central chest (pectus carinatum); (3) an entire chest that slopes inward toward the abdomen without a level plane; (4) asymmetry; and (5) other chest irregularities that interfere with the position of an underwire. In all these cases, firmly and evenly opposing a bra underwire on the chest wall is difficult or impossible no matter how tight the back strap of the bra is fastened. Infinite variabilities of chest wall shape leave many users without a viable solution, both women desiring breast support and surgeons wanting to influence post-operative implant position.

Another challenge for mass-produced bras for the breast implant patient is that such bras are designed for natural breasts. Implanted breasts are different in that they do not add much volume in the sternum area but add it more in the breast meridian or in the central breast area. Therefore, the connection between the underwire and cups of a mass-produced bra is often not long enough, with the result being that the area of the underwire does not fit correctly to the chest.

BRIEF DESCRIPTION OF THE DRAWINGS

These and/or other aspects will become apparent and more readily appreciated from the following description of the embodiments, taken in conjunction with the accompanying drawings of which.

Figure 1:
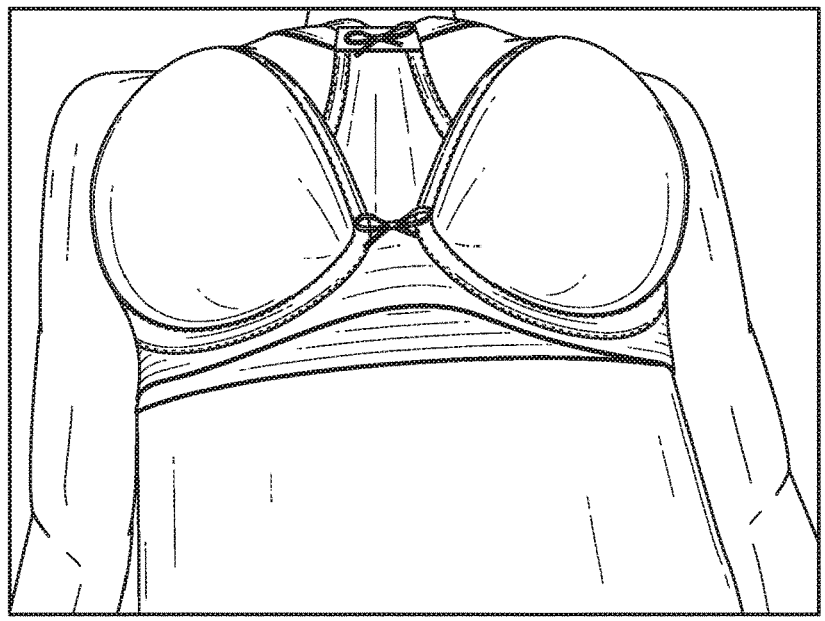
FIG. 1 illustrates an example of an existing breast separator worn in conjunction with a bra.

The headings provided herein are for convenience only and do not necessarily affect the scope or meaning of what is claimed in the present disclosure.

Embodiments of the present disclosure and their advantages are best understood by referring to the detailed description that follows. It should be appreciated that like reference numbers are used to identify like elements illustrated in one or more of the figures, wherein showings therein are for purposes of illustrating embodiments of the present disclosure and not for purposes of limiting the same.

DETAILED DESCRIPTION

In an embodiment, a chest wall adapter apparatus for supporting a user's breasts includes a right section and a left section, wherein the right section and the left section are contiguous on a front side of the apparatus. The apparatus also includes an inwardly extending convex portion located between the right section and the left section, wherein the inwardly extending convex portion is configured to lie against the chest wall of the user between the breasts; a horizontally extending and upwardly angled right shelf configured to extend along the right section and follow a contour along an underside of a right breast of the user; a horizontally extending and upwardly angled left shelf configured to extend along the left section and follow a contour along an underside of the left breast of the user; a vertically extending adapter wall, having an inner face and an outer face, a top of the vertically extending adapter wall is integrally formed with the shelf and defines a curved edge corresponding to an inframammary fold of the breasts of the user, the inner face is configured to lie against the user's chest wall beneath the breasts of the user; a right thorax extension that extends from the right section on a rear side of the apparatus so as to wrap at least partially around a thorax of the user; and a left thorax extension that extends from the left section on a rear side of the apparatus so as to wrap at least partially around a thorax of the user.

In other embodiments, the apparatus includes a right stabilization prong that extends upwardly from the right section so as to wrap at least partially around a top of a right breast of the user, and a left stabilization prong that extends upwardly from the left section so as to wrap at least partially around a top of a left breast of the user.

According to an embodiment, a chest wall adapter apparatus for supporting a user's breasts includes a right section and a left section, wherein the right section and the left section are contiguous on a rear side of the apparatus via a back supporting piece, and wherein the right section and the left section a separated by a gap on a front side of the apparatus. The apparatus also includes a connector spanning the gap, wherein the connector is adjustable to allow the user to change the width of the gap; a horizontally extending and upwardly angled shelf configured to extend along the left section and the right section and follow a contour along at least an underside of the breasts of the user; a vertically extending adapter wall, having an inner face and an outer face, a top of the vertically extending adapter wall is integrally formed with the shelf and defines a curved edge corresponding to an inframammary fold of the breasts of the user, the inner face is configured to lie against the user's chest wall beneath the breasts of the user; a left stabilization prong that extends upwardly from the left section so as to wrap at least partially around a top of a left breast of the user when worn; and a right stabilization prong that extends upwardly from the right section so as to wrap at least partially around a top of a right breast of the user when worn.

A convex portion having a shape corresponding to a depression in the chest wall of the user, or a concave portion having a shape corresponding to a prominence in the chest wall of the user.

The shelf has a width in a direction substantially perpendicular to the lip, the width varying between a center point of the apparatus and a lateral end of the apparatus.

The shelf has a width in a direction substantially perpendicular to the lip, the width gradually decreasing as the shelf extends laterally outward from a center point of the apparatus.

In an embodiment, the shelf has a width in a range of 0.5 to 2.0 inches in a direction substantially perpendicular to the lip. In other embodiments, the shelf is more than 2.0 inches in a direction substantially perpendicular to the lip.

The lip extends 1.0 to 2.0 or less inches from the point of intersection with the shelf.

The shelf is configured to be anchored by the underwire of a bra.

The lip has an inner face and an outer face, the inner face configured to stabilize the chest wall adapter apparatus against the chest wall of the user.

The shelf is configured to extend along an underside of two breasts of the user, and the curved edge corresponds to a contour of an inframammary fold of each breast.

A first portion of the shelf extends along the underside of one breast along a first horizontal plane and a second portion of the shelf extends along the underside of another breast along a second horizontal plane different than the first horizontal plane.

In another embodiment, a method for managing settling of a breast implant of a user includes obtaining a three-dimensional rendering of a chest wall and at least one breast of the user; using the three-dimensional rendering to generate a chest wall adapter device for the user, the chest wall adapter device having (i) a shelf configured to extend along an underside of the at least one breast of the user so as to correspond to a contour of the underside of the at least one breast, and (ii) a lip integrally formed with the shelf and extending in a direction substantially perpendicular to the shelf, the lip configured to press against the chest wall of the user at a location beneath the at least one breast, wherein the intersection of the shelf and the lip forms a curved edge corresponding to a contour of an inframammary fold of the at least one breast of the user; and applying the chest wall adapter device to manage settling of at least one breast implant of the user.

In other embodiments, the method for managing settling of a breast implant of a user further includes one of, or any suitable combination of two or more of, the following features.

The three-dimensional rendering of the chest wall and the at least one breast of the user is obtained in response to determining that a condition has been satisfied following completion of breast augmentation or reconstruction surgery. It is to be understood, however, that three-dimensional printing can vary considerably from the true three-dimensional image, since computer renderings can be made for devices of many different shapes and sizes and the final choice will depend in part on the goals for any given patient.

Determining that a condition has been satisfied following completion of breast augmentation or reconstruction surgery includes one of (i) determining that a threshold period of time has elapsed following the completion of breast augmentation or reconstruction surgery and (ii) determining that a threshold amount of settling has occurred for the at least one breast implant of the user.

The threshold period of time is five weeks following the completion of breast augmentation or reconstruction surgery.

The three-dimensional rendering of the chest wall and the at least one breast of the user is one of (i) a three-dimensional image of the chest wall and the at least one breast of the user and (ii) a three-dimensional solid model drawing of the chest wall and the at least one breast of the user.

In another embodiment, a method for manipulating a shape of a breast of a user includes obtaining a three-dimensional rendering of a chest wall and at least one breast of the user; using the three-dimensional rendering to generate a chest wall adapter device for the user, the chest wall adapter device having (i) a shelf configured to extend along an underside of the at least one breast of the user so as to correspond to a contour of the underside of the at least one breast, and (ii) a lip integrally formed with the shelf and extending in a direction substantially perpendicular to the shelf, the lip configured to press against the chest wall of the user at a location beneath the at least one breast, wherein the intersection of the shelf and the lip forms a curved edge corresponding to a contour of an inframammary fold of the at least one breast of the user; and applying the chest wall adapter device to manipulate a shape of the at least one breast of the user.

Obtaining a three-dimensional rendering of a chest wall and at least one breast of the user includes scanning the chest wall and the at least one breast of the user using a three-dimensional scanner.

Using the three-dimensional rendering to generate a chest wall adapter device for the user includes using a three-dimensional printer to generate the chest wall adapter device based on digital rendering data associated with the three-dimensional rendering.

Further scope of applicability of the apparatuses and methods of the present disclosure will become apparent from the more detailed description given below. However, it should be understood that the following detailed description and specific examples, while indicating embodiments of the apparatus and methods, are given by way of illustration only, since various changes and modifications within the spirit and scope of the concepts disclosed herein will become apparent to those skilled in the art from the following detailed description.

Various examples and embodiments of the present disclosure will now be described. The following description provides specific details for a thorough understanding and enabling description of these examples. One of ordinary skill in the relevant art will understand, however, that one or more embodiments described herein may be practiced without many of these details. Likewise, one skilled in the relevant art will also understand that one or more embodiments of the present disclosure can include other features and/or functions not described in detail herein. Additionally, some well-known structures or functions may not be shown or described in detail below, so as to avoid unnecessarily obscuring the relevant description.

One or more embodiments of the present disclosure include a chest wall adapter device for supporting at least one breast of a user. The chest wall adapter device has a stiff, anatomically-shaped construction designed to fit a user's chest shape and provide an optimal amount of pressure to the inframammary fold areas of the user's chest. As will be described in greater detail below, the chest wall adapter device of the present disclosure is a revolutionary step forward in implant position control post-operatively and also breast support. In some examples, the post-operative breast support includes providing control to breast implants following breast implant surgery or another breast augmentation or reconstruction procedure.

As used herein, the terms "user," "person," and "patient" may be used interchangeably, and refer to an individual that may utilize the chest wall adapter device described herein. In some examples, the user may be an individual who has undergone some form of a medical procedure that involved or impacted their breasts and/or chest. As used herein, a "bra" or "brassiere" is used in its plain and ordinary meaning as a form-fitting undergarment designed to support an individual's breasts.

Figure 4:
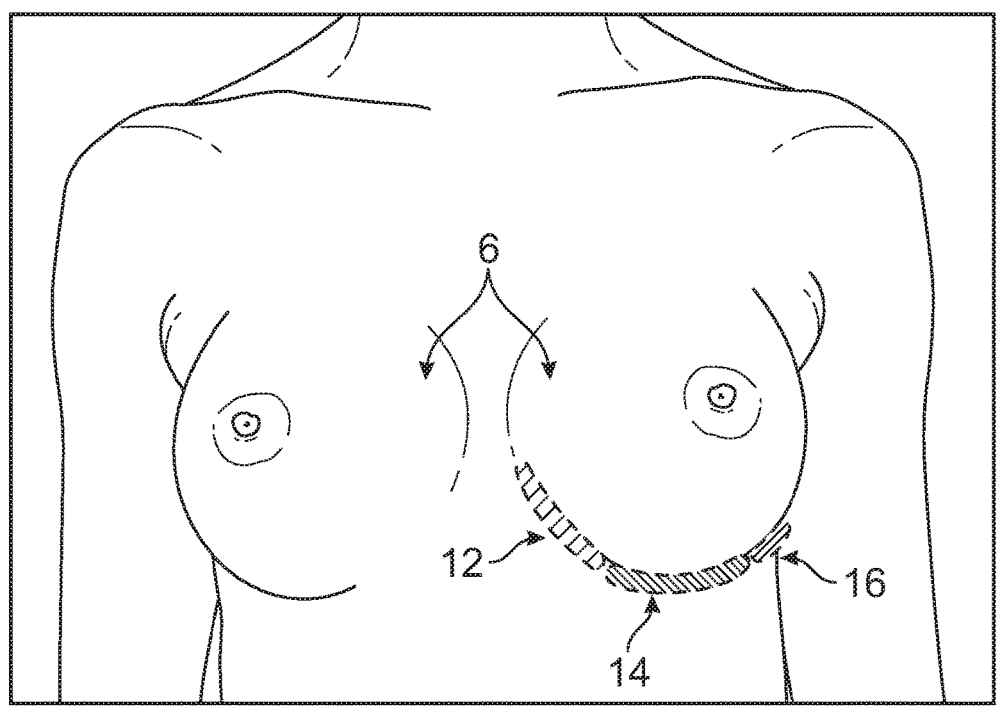
FIG. 4 illustrates key sections of the inframammary fold of the breast.
Figure 5:
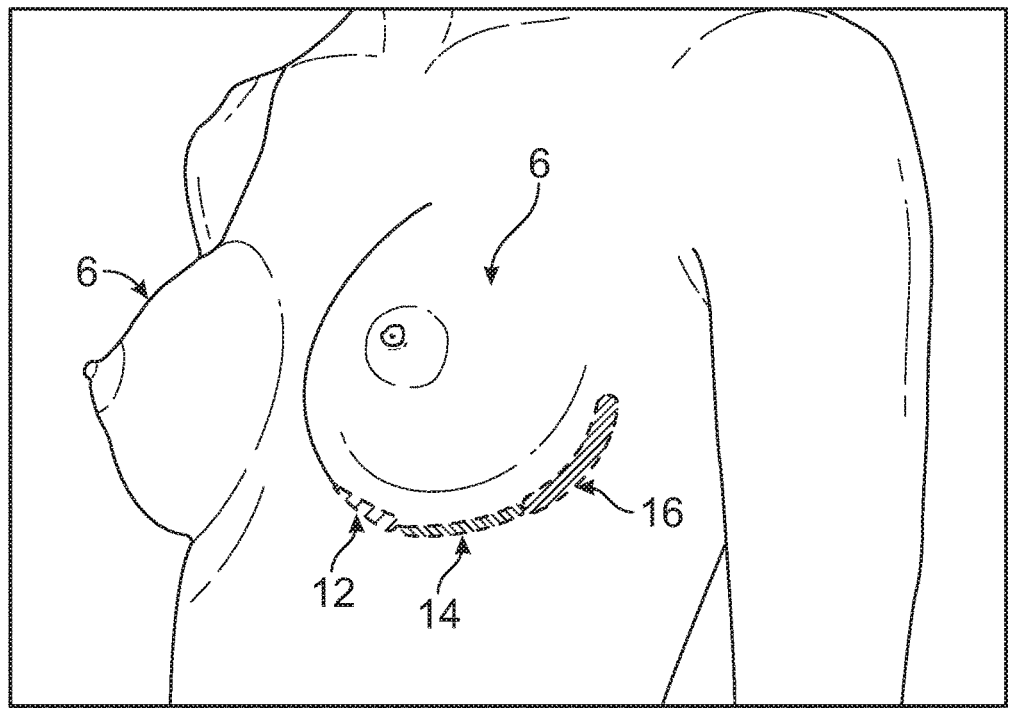
FIG. 5 illustrates a side view of the key sections of the inframammary fold.

FIGS. 4 and 5 show an example breast including the inframammary fold. The inframammary fold is the anatomical boundary formed at the lower (or inferior) border of the breast 6, where the breast 6 joins with the chest wall. Here, for the purposes of controlling implant position, the inframammary fold will be divided into three sections, the sternal inframammary fold 12, meridian inframammary fold 14, and lateral inframammary fold 16. As will be described in greater detail below, the chest wall adapter device of the present disclosure is designed to specifically provide pressure to these areas of the inframammary fold, namely, the sternal inframammary fold 12, meridian inframammary fold 14, and lateral inframammary fold 16, as pressure to these areas of the chest wall 6 are important to prevent settling of breast implants downward or migration of breast implants toward the middle of the chest (medial displacement or synmastia) or migration of breast implants toward the side of the chest following surgery.

In accordance with one or more embodiments, the chest wall adapter device and methods of utilizing the chest wall adapter device described herein are designed to counteract the breast implant settling process that occurs following breast implant surgery. In at least some embodiments, the chest wall adapter device and methods of use allow a person to reliably control the usual but somewhat unpredictable downward settling of breast implants during the period following submuscular breast augmentation, and thereby achieve a more desirable shape and positioning for life.

In at least some embodiments, the chest wall adapter device is used as a post-operative support mechanism to prevent breast implants from sliding downward (sometimes referred to as "settling" or "dropping"), which typically occurs for approximately six or seven months following breast reconstruction or augmentation surgery.

In the early seven months following breast implant surgery, before a tough resistant capsule has formed and matured, the implant position can potentially be manipulated. Many patients wish for their breast implants to be closer together for better "cleavage." In accordance with some embodiments, the chest wall adapter device can be altered to apply pressure to the outside of the breast pushing the implants toward the center of the chest. Depending on the amount of desired cleavage, it may be necessary to periodically reproduce or reconfigure the chest wall adapter device so to maintain the requisite side or "lateral" pressure. Presently, if a user wants their breasts to appear closer together, the only option for submuscular implants is fat grafting to the area between the breasts, which is costly and also performed under general anesthesia. Some patients with depressions in the middle of their chests (pectus excavatum) need the device configured to push the implants apart.

Often, patients will have narrow chests that are very sloped to the side. Inherently in these cases breast implants sit on a ramp sloped to the side of the chest. In some of these patients, the implants will gradually fall to the side of the chest, which is especially bothersome when the patients lie on their back and while they are sleeping it can even be uncomfortable. In some patients only one side of the chest is narrow and that tends to be the problematic side with drift or migration of the breast implant. In accordance with some embodiments, the chest wall adapter device can be produced (e.g., printed) and/or configured to support the side of one or both breasts.

The submuscular breast implant technique, performed since the 1970s, has offered many advantages to breast implant surgery including, for example, providing more padding over the implant, a more natural appearance, better quality mammograms, long term stability, and low incidence of capsule contracture. A disadvantage of the technique is that implants settle downward for six to seven months following surgery and the amount of downward settling during this time varies with tissue elasticity, chest wall shape, size of the implant, activities of the person, and technique of the surgeon. In other words, final implant position is not totally predictable. Research and literature on the topic indicates reoperation rates for primary breast augmentation as high as 36% with a significant portion of these cases "malposition." At the Baker Gordon Symposium in Miami February 2017, speaker Dr. Bradley Calabrace stated that final postoperative implant position is "in the hands of God . . . ." Dr. Calabrace proposes the use of textured implants to control final implant position as their rough surface does not slide downward as much. However, Dr. Calabrace's approach is heavily criticized at present due to the recent discovered association of textured implants with Anaplastic Large Cell Lymphoma (ALCL). *Breast Implant Informed Consent Should Include the Risk of Anaplastic Large Cell Lymphoma*, Clemens et al., Plastic and Reconstructive Surgery, Vol. 137, No. 4 Apr. 2016. In some embodiments, the chest wall adapter device is applied to the setting of smooth breast implants. However, it should be understood that the chest wall adapter device would function with textured implants as well.

Breast implants placed beneath the muscle change for several months following surgery. For example, implants continue to drop day-by-day during the first seven months, and possibly longer with larger implants. Properly placed breast implants (both gel and saline implants) slide downward on the chest for six to seven months after surgery. For some individuals a certain amount of settling of the implants is desired. However, such settling often goes beyond what is desirable or aesthetically pleasing. Many patients wish to minimize any subsequent settling of the implants beyond a certain chosen look. Since the downward sliding of the implants occurs gradually following surgery, most patients are unaware that it is happening at all until the later months when they frequently express their disappointment that the implants are not as high up on their chests as they once were.

It appears that breast implants that are dropping are "peeling away" skin off the lower chest and upper abdomen. In other words, the skin is lifted up away from the body with the weight of the implant pushing down. It is a matter of fluid mechanics with either the liquid (saline) or semiliquid (gel) exerting pressure into the newly created lower space transmitted into upward lift on the skin propagating further the process. The implants typically stop descending by seven months after surgery, once the person's body forms a tougher tissue around the implant called a "capsule."

Figure 6:
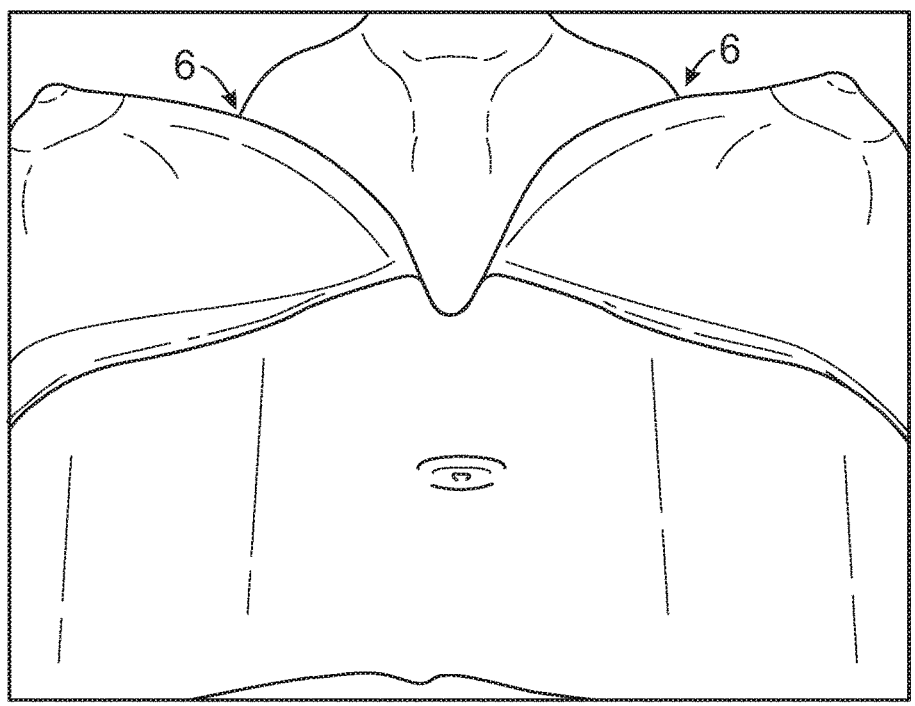
FIG. 6 illustrates an example of the depressed central chest of pectus excavatum.
Figure 7:
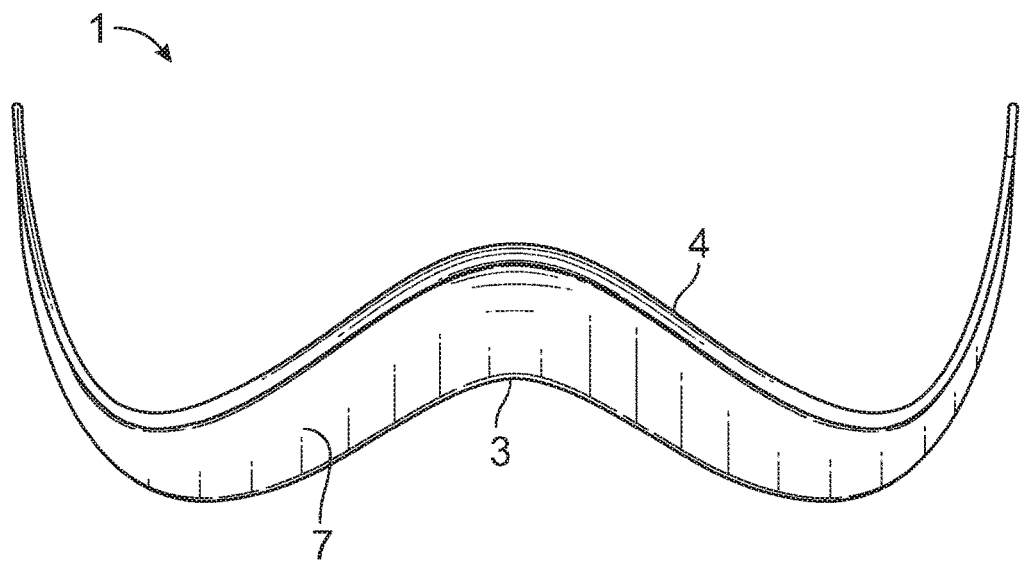
FIG. 7 illustrates a front view of a chest wall adapter device, according to an embodiment.
Figure 8:
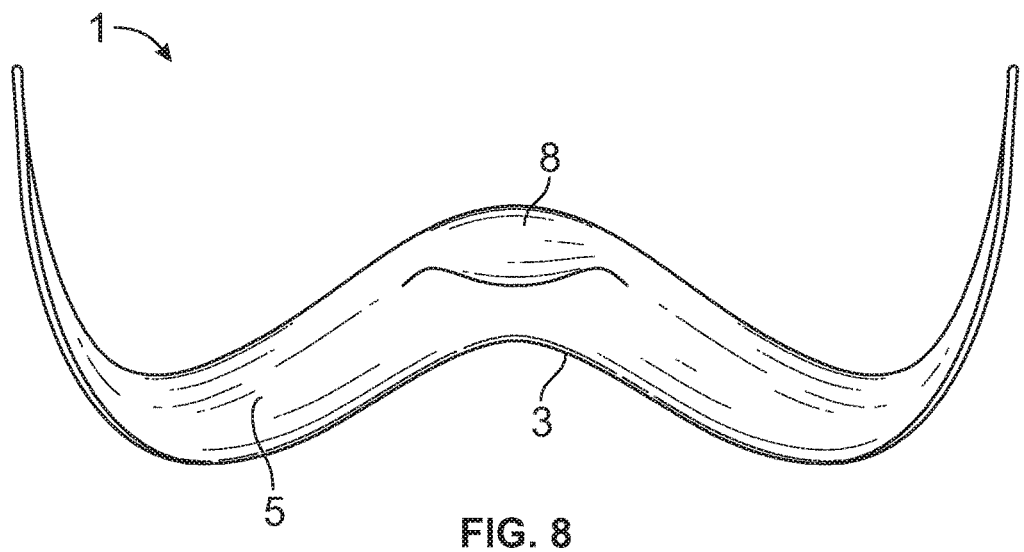
FIG. 8 illustrates a back view of the chest wall adapter device shown in FIG. 7, according to an embodiment.
Figure 9:
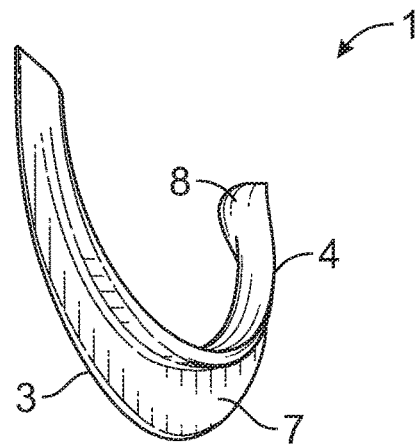
FIG. 9 illustrates a right side perspective view of the chest wall adapter device shown in FIG. 7, according to an embodiment.
Figure 10:
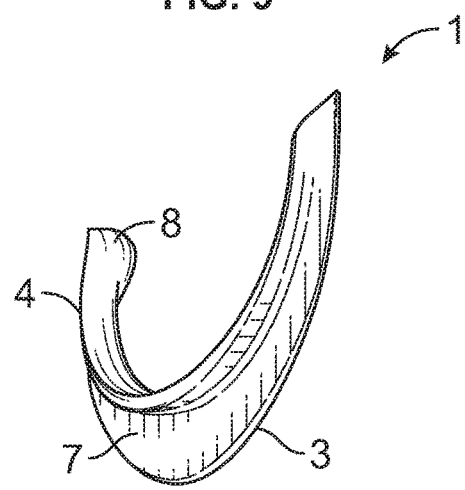
FIG. 10 illustrates a left side perspective view of the chest wall adapter device shown in FIG. 7, according to an embodiment.
Figure 11:
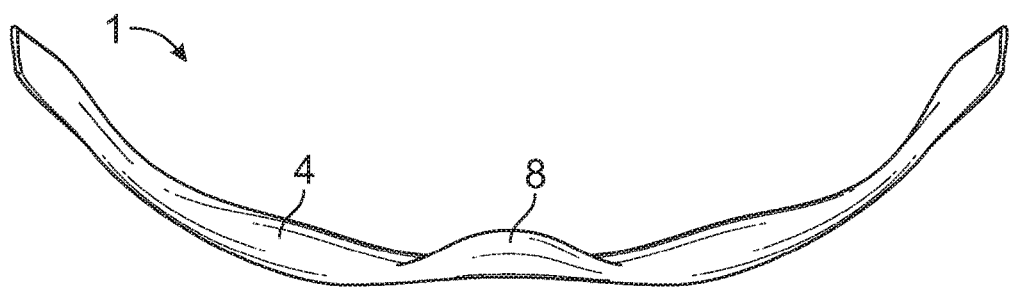
FIG. 11 illustrates a top view of the chest wall adapter device shown in FIG. 7, according to an embodiment.

FIG. 1 illustrates an example of the easily-purchased breast separator apparatus that is worn to apply pressure on the sternal inframammary fold area in an attempt to inhibit implants from sliding together in the midline. Patients with a caved-in central chest (pectus excavatum) are especially at risk for this problem. Implants in the early months especially, will slide down the prevailing slope: toward the middle of the chest in those cases of pectus excavaturm, but more commonly toward the side of the chest as the slope tends to be there. Breast separators are weak and ineffective but a firm pressure on the skin in the area of the sternal inframammary fold will stop a migration toward the middle. Similarly firm pressure on the skin at the lateral inframammary fold will stop the outward migration. FIG. 6 shows an example of a depressed area in the chest wall of a user between the breasts 6. A breast separator does not have the power needed to prevent breast implants from settling toward the middle of the chest. The breast separator applies pressure over a wide area of the chest, not at the advancing edge of an implant and thus is ineffective.

Figure 2:
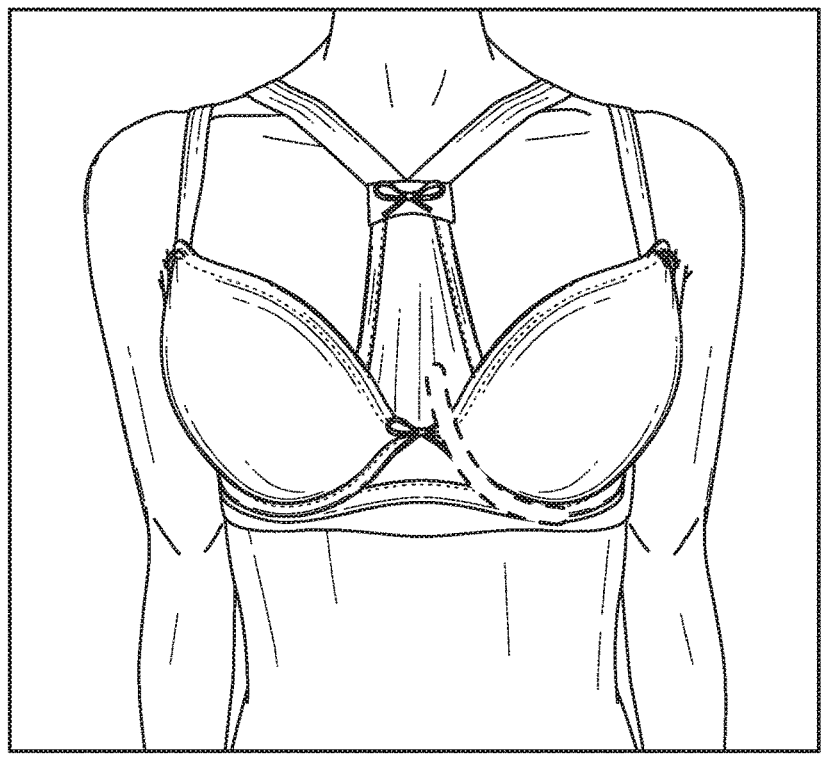
FIG. 2 illustrates another example of an existing breast separator worn in conjunction with a bra.

FIG. 2 shows another example of a breast separator beneath a bra. The area marked by broken lines depicts where firm localized pressure is needed for effectiveness and this corresponds to the sternal inframammary fold. The topography here is unique for every patient, and so only a device produced in a customizable manner (e.g., 3D printed) could consistently apply pressure where needed.

Figure 3:
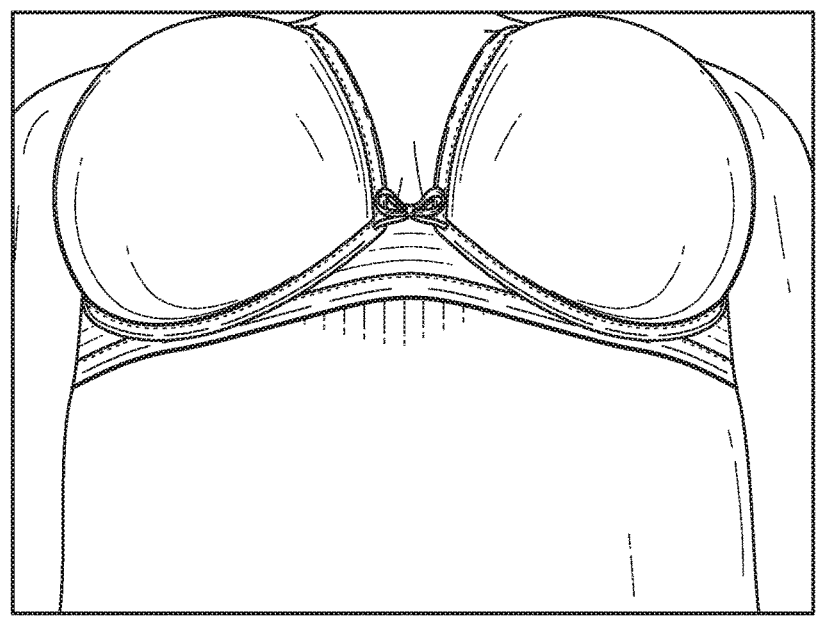
FIG. 3 illustrates another example of an existing bra in which the underwire of the bra is lifted away from the surface of the skin.

FIG. 3 shows an example of an existing bra that has an underwire failing to follow the unique surface topography of the inframammary fold. As represented by the shadow lines that appear on the user's chest wall beneath the bridge of the bra, the bra's underwire is lifted away from or not touching the skin. As a result, the bra does not provide the needed support to the breast. More importantly, however, the underwire of the bra fails to provide pressure where needed to the sternal and meridian inframammary folds of the breast. With such a configuration, the bra's underwire cannot function to achieve the unique postsurgical goal of providing pressure to the inframammary fold to prevent breast implants from settling or permanently migrating.

In view of the challenging situations shown in FIGS. 1-3 and described above, there is a demonstrated need for a chest wall adapter device and method of use that can externally manipulate, resist, and even arrest settling of breast implants during the postoperative period. No such device presently exists. Bras and other similar support mechanisms usually fail in any attempt surgeons and/or patients make for a number of reasons including, but not limited to, the following: (1) there is no understanding of how bras could potentially work even if of the right type and with average-shaped chest; (2) as surgeons are not aware of the mechanism of action, patients are not instructed on what type of firm underwire bra to purchase and how it should be worn during all waking hours; (3) most patients do not get professional bra fitting and even if they do it is aimed at manipulating the breast tissue with no one involved understanding the very different means of manipulating an implant; (4) the vast majority of bras purchased do not have a firm, strong, well-fitted underwire; (5) many patients have chest shapes that cannot be accommodated by mass-produced bras; (6) some patients have wide breasts with much cleavage over the breast bone that resists and displaces away the medial (sternal side) underwire of a bra; (7) even with an understanding of the mechanism of action, many patients will resist having a cup that is slightly large; with patients pressuring the fitter for a tight (better look) cup, the result is the breast slightly overfilling the cup and thus pushing the entire bra forward and lifting the underwire away from the skin thwarting any attempt to apply pressure to the skin in the area of the inframammary fold. In accordance with some embodiments, a 3D printed device can overcome these many challenges even in unusually-shaped chests. In some embodiments, a chest wall adapter device is configured so that one site of pressure on the device beneath each breast by an overlying underwire bra or other mechanism to hold the device in place is all that is needed for the appropriate amount of pressure to be applied at the key sections of the inframammary fold.

In some embodiments, the chest wall adapter device is designed to be utilized in conjunction with one or more other apparatuses typically worn by a user to provide support for the breasts. For example, the chest wall adapter device may be used in conjunction with a bra, body strap, or band, which secures the chest wall adapter device to the chest of the user. The chest wall adapter device fits snugly against the user's chest wall, sternal inframammary fold, meridian inframammary fold, and lateral inframammary fold, and is held securely in place by the bra, body strap, band, or combination thereof. In such instances, shoulder straps may optionally be worn to provide even further support and direct the applied pressure as needed.

In one or more embodiments in which the chest wall adapter device is used in conjunction with a bra, the shoulder straps of the bra, which travel over the shoulders of the user, are configured to be tight enough to stabilize the bra. Any more tightness will in effect pull the bra's underwire away from the chest, thereby reducing the effectiveness of the chest wall adapter device. In at least one embodiment, the chest wall adapter device may be configured for use with a bra and additional straps or a band that attaches to the bra or to the support device and extends around the user's back to provide additional stability to the support device. Such additional straps or a band may be useful for a user with an irregular or unusual chest shape.

In at least one embodiment, the chest wall adapter device is first utilized at the end of a period of time following breast implant surgery. For example, a user may begin to use the chest wall adapter device (or a doctor or medical practitioner may direct a user to begin using the chest wall adapter device) after a period of eight weeks following the completion of breast implant surgery. In another example, this period of time following the completion of breast implant surgery may be shorter (e.g., four weeks, six weeks, etc.) or longer (e.g., ten weeks, fourteen weeks, etc.) than eight weeks, depending on the preferences of the user, the particular characteristics of the user's chest, any medical conditions, or the like. In an embodiment, the chest wall adapter device is first used to arrest the settling of breast implants between a period of four to eight weeks following the completion of breast implant surgery.

In some embodiments, the chest wall adapter device is used (e.g., worn, applied, etc.) by the user for a period of approximately six months following the first use of the device by the user, during which time the chest wall adapter device acts to prevent the settling of breast implants in the user. In at least one embodiment, the breast support device is utilized for a continuous period of between five and six months following the first use of the device by the user. The period of time during which the chest wall adapter device is to be utilized by the user is measured from the first use of the device by the user, according to some embodiments. In other embodiments, the period of time during which the chest wall adapter device is to be utilized by the user is measured from the completion of breast implant surgery. In some embodiments, during the period of time in which the chest wall adapter device is to be utilized by the user, the chest wall adapter device is used intermittently or according to some predetermined schedule. In some embodiments, during the period of time in which the chest wall adapter device is to be utilized by the user, the chest wall adapter device is used continuously throughout the period of time.

The permanent result in the appearance of a breast implant is primarily determined in the first six to seven months following breast implant surgery. Controlling the implant level during this initial healing period is important because, after six to seven months, the final location where the breast implant settles will usually not significantly change for many years or even decades. While there are exceptions to this general understanding, including, for example, cases involving larger implants, unusual chest shapes, and certain upper body workouts, these are the exceptions, not the rule. In general, breast implants do not move after seven months following the completion of breast implant surgery because the body produces a "capsule" to hold the implants in place, and this capsule has considerable strength at seven months post-surgery.

In an embodiment, the chest wall adapter device 1 is configured to precisely follow the contour of the intersection between the user's breasts and the user's chest. In this manner, the chest wall adapter device 1 provides optimal support to the breasts or the implants of the user and is comfortable for the user to wear. In some embodiments, the chest wall adapter device 1 is configured to precisely follow the contour of the intersection between the user's breasts and the user's chest even if the user's chest has one or more irregularities such that one side of the user's chest is different from the other side.

The chest wall adapter device 1 is molded and constructed to stop migration of implants at consistent locations on both sides of a user's chest, even if the chest wall is uneven or the breasts are uneven. For example, in an embodiment, the chest wall adapter device 1 is configured to support the breasts along the same horizontal plane with respect to the user's chest. In another embodiment, the chest wall adapter device 1 is configured to support the user's breasts at different horizontal planes (e.g., at different heights on the user's chest when the user is standing upright). For example, the chest wall adapter device 1 may be configured to support one side's implant at a first height on the user's chest and another implant at a second, different height on the user's chest. This could be useful if adjusting an asymmetry. Providing support to a user's implants at varying heights may be desirable to achieve the best overall appearance of the breasts.

It should be noted that the chest wall adapter device 1 may be configured to support various sizes and/or shapes of breasts and breast implants, depending on the particular anatomical characteristics of the user and/or the particular desires of the user. For example, in one embodiment, the chest wall adapter device 1 includes a convex portion or concave portion 8 having a shape corresponding to the anatomical shape or structure of the user's chest wall. While portion 8 of the chest wall adapter device 1 will be referred to herein as the convex portion, it should be understood that in some embodiments, portion 8 is a concave portion having a shape to complement a corresponding anatomical shape or structure of the user's chest wall. The convex portion 8 may be configured, for example, to complement a user having a concave chest wall (pectus excavatum). With a perfect hand-in-glove fit there is much more stability, the ability to apply pressure where needed and in supporting breast tissue or stabilizing implants the device is anchored in a stable fashion on the chest and thus can be much more supportive. It is very difficult to provide adequate support to a user's breasts and breast implants when the user has a depressed or concave chest wall. As such, the convex portion 8 of the chest wall adapter device 1 is configured to follow any degree of depression in the user's chest wall to remain stable and anchored to provide maximum support to the user's breasts and breast implants. It should be noted that most individuals have at least a slight depression in their chest wall or a prominence such as in the center of the chest (pectus carinatum). The chest wall adapter device 1 may be configured to have a convex or concave portion 8 of various size and shape to complement the particular anatomical characteristics of the user's chest wall, according to an embodiment.

FIGS. 7-11, 12A, and 13A illustrate an example chest wall adapter device 1 in accordance with some embodiments of the present disclosure. In at least one embodiment, the chest wall adapter device 1 is a single article having a customized shape and form corresponding to the specific anatomical shape and contours of the user's chest and at least one breast. The chest wall adapter device 1 has a shelf or ledge 4 which extends substantially perpendicular to the chest wall and along the underside of the breast 1. The shelf 4 has a shape that matches the contour of the underside of the user's breast or breasts. In an embodiment, a width of the shelf 4 varies between a center point of the chest wall adapter device 1 and the lateral ends of the chest wall adapter device 1. For example, a width of the shelf 4 may gradually decrease as the shelf 4 extends laterally outward from the center of the chest wall adapter device 1. In one embodiment, the width of the shelf 4 may be substantially uniform at all points along the chest wall adapter device 1. The chest wall adapter device 1 also includes a downward-extending lip 3 having a contour corresponding to that of the user's chest wall below at least one of the user's breasts. An edge is formed at the intersection of the downward-extending lip 3 and the shelf 4 of the chest wall adapter device 1, and this edge follows the contour of the user's inframammary fold. In this position with overlying pressure from the underwire of a bra, migration of an implant can be stopped in at least three directions: medially, downward, and laterally as pressure will be transmitted to the medial inframammary fold, meridian inframammary fold, and lateral inframammary fold. It is also in this position of stability that the chest wall adapter device 1 can support parts of the breast itself with extensions of the shelf 4. In at least one embodiment, the downward-extending lip 3 has an inner face or surface 5 and an outward face or surface 7. The inner face 5 may be configured to stabilize the chest wall adapter device 1 against the user's chest and/or ribs while the outward face 7 may be configured to receive or attach to one or more other support devices or mechanisms (e.g., a bra). In an embodiment, the shelf 4 may be configured to anchor (e.g., receive, attach to, be fitted with, etc.) the underwire of a bra, such that the underwire of the bra sits beneath the shelf 4 against the outward face 7 of the lip 3. In this manner, the underwire of the bra exerts pressure against the underside of the shelf 4 to stabilize the chest wall adapter device 1.

Figure 14:
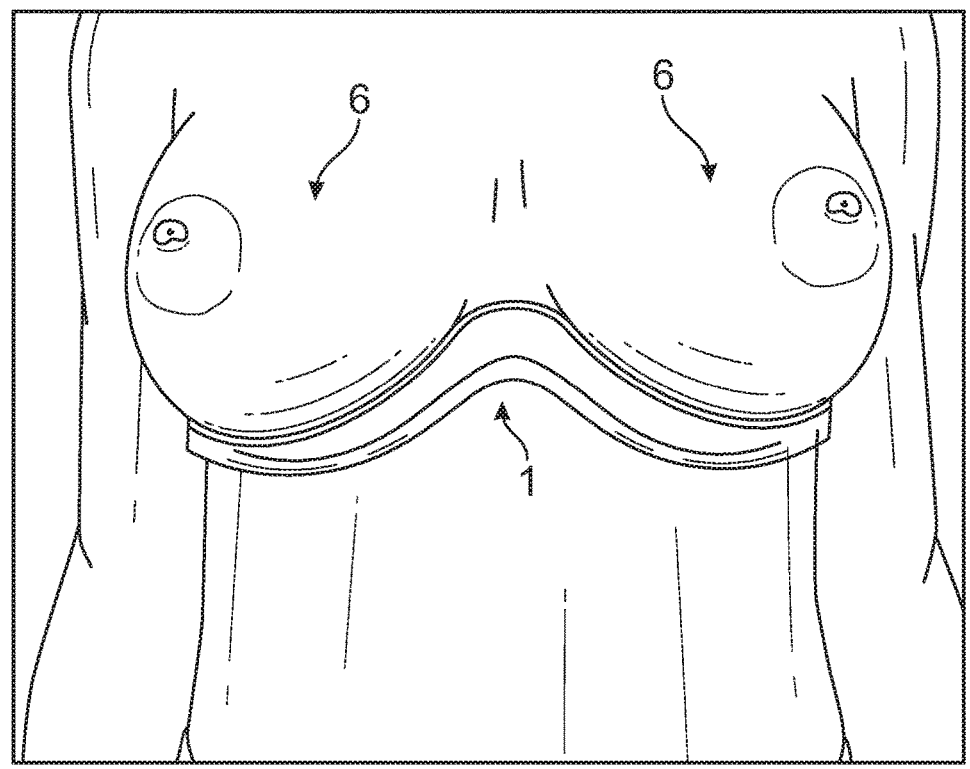
FIG. 14 illustrates a chest wall adapter device adapted to the unique chest wall shape of a user, the chest wall adapter device in position to apply pressure to the key sections of the inframammary fold, according to an embodiment.
Figure 15:
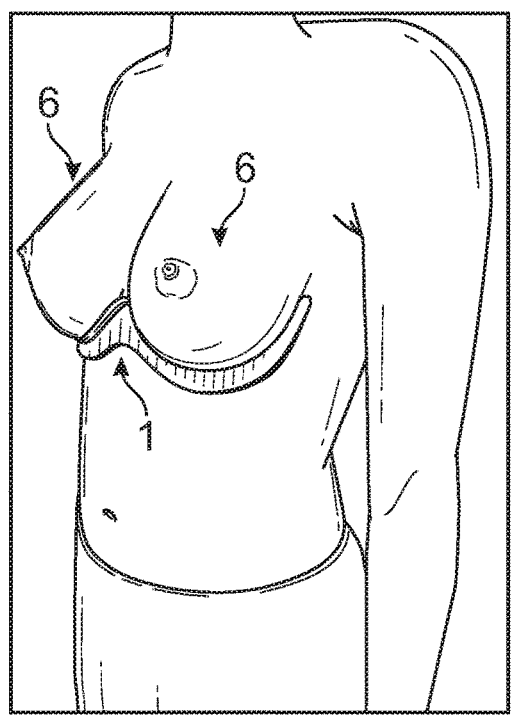
FIG. 15 illustrates a perspective oblique view of a chest wall adapter device, in position to apply pressure to the key sections of the inframammary fold, according to an embodiment.

FIGS. 14 and 15 illustrate an example chest wall adapter device 1 providing support to the implants and breasts 6 of a user. In some embodiments, the shelf 4 extends outward from the user's chest when the chest wall adapter device 1 is being utilized. The shelf 4 is configured to fit under or beneath at least one breast so as to cradle the breast and provide stability to the breast. Such an extension of the device medially can push, manipulate, or lift the inside or medial aspect of a user's breast. Some users have breasts spillage medially that bras cannot seem to control. A customized lip 4 can provide control to this area, according to some embodiments.

In some embodiments, the shelf 4 may extend 0.5 to 2.0 inches outward from the user's chest when the chest wall adapter device 1 is in use. In another embodiment, the shelf may 4 extend outward from the user's chest by a length outside the range of 0.5 to 2.0 inches. The shelf 4 extends in a direction substantially perpendicular to a vertical plane of the chest wall adapter device 1 when in position for use by a user, according to an embodiment.

The chest wall adapter device 1 may have a curved surface at the point where the shelf 4 meets the downward-extending lip 3, according to an embodiment. This curved portion may be configured to exert pressure precisely at the user's inframammary fold. For added stability, the downward-extending lip 3 may extend 1.0 to 2.0 inches down from the point of intersection with the shelf 4, in an embodiment. In one or more other embodiments, the lip 3 may extend down by a length outside of the range of 1.0 to 2.0 inches, depending on the particular anatomical characteristics of the user's chest.

Figure 18:
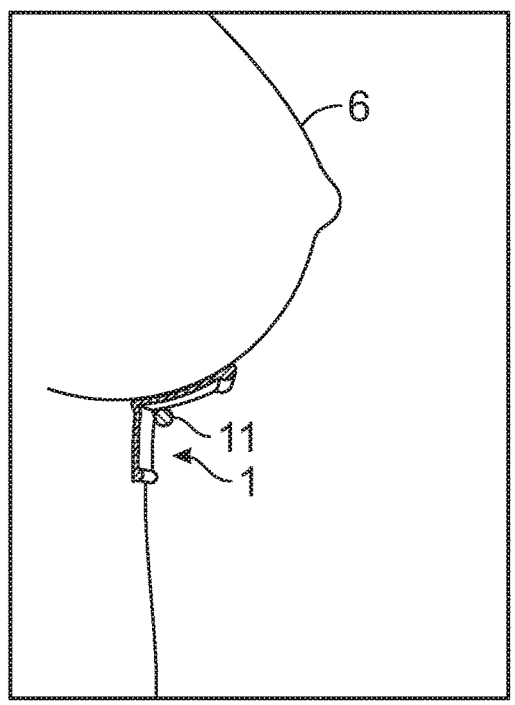
FIG. 18 illustrates a cross-sectional side view of a chest wall adapter device with an underwire of a bra in position to apply pressure to the chest wall adapter device, according to an embodiment.

FIG. 18 is a cross-sectional side view of the chest wall adapter device 1. From the perspective shown, the chest wall adapter device 1 may be L-shaped, V-shaped, or U-shaped to provide appropriate stabilization and support to the user's breast or implants, in an embodiment. In such a configuration, the downward force exerted by the user's breasts and breast implants is counteracted by the stability of the downward-extending lip 3 pressing against the chest wall. In this manner, the chest wall adapter device 1 is designed to apply pressure against the user's rib cage and chest to support the breasts and breast implants. In at least one embodiment, the downward-extending lip 3 is configured to precisely fit the user's chest wall so as to provide maximum support and comfort for the user.

In one embodiment, the chest wall adapter device 1 is configured to be highly stabilized against the user's chest to provide substantially equal support to both the user's left and right breast from a central point over the sternum or breast bone. In this manner, the chest wall adapter device 1 may be configured to function in a variety of ways. For example, the shelf 4 of the chest wall adapter device 1 that extends along the underside of the breast can be made longer on one or both sides, providing support for shaping and/or pushing the breast that is not possible with bra underwires, shoulder straps, or other existing support mechanisms.

In one embodiment, the chest wall adapter device 1 device can be configured with a separate strap that extends around the chest and there may also be attached shoulder straps. In another embodiment, the chest wall adapter device 1 can have a strap that extends around the user's back but has no cup in the front.

In one embodiment, the chest wall adapter device 1 is integrally formed with a bra 10 into a single support device. The combination of the chest wall adapter device 1 and bra 10 provides a stiff, anatomically-shaped support mechanism that fits exactly to a user's chest and provides vertical and lateral support for the breasts and breast implants. The support apparatus consisting of the chest wall adapter device 1 and bra 10 provides support to the user's breasts and breast implants at the three particular locations (e.g., at three pillars of resistance): 1) the sternal inframammary fold, 2) the meridian inframammary fold, and 3) the lateral inframammary fold. The chest wall adapter device 1 is designed to account for variability in the chests and breasts of different users, such that the device cradles the breasts and breast implants in a consistent location on each user's chest. If used after breast augmentation surgery, the chest wall adapter device 1 controls the implant position while the capsule forms and the tissue strengthens to hold the implants in place.

Figure 16:
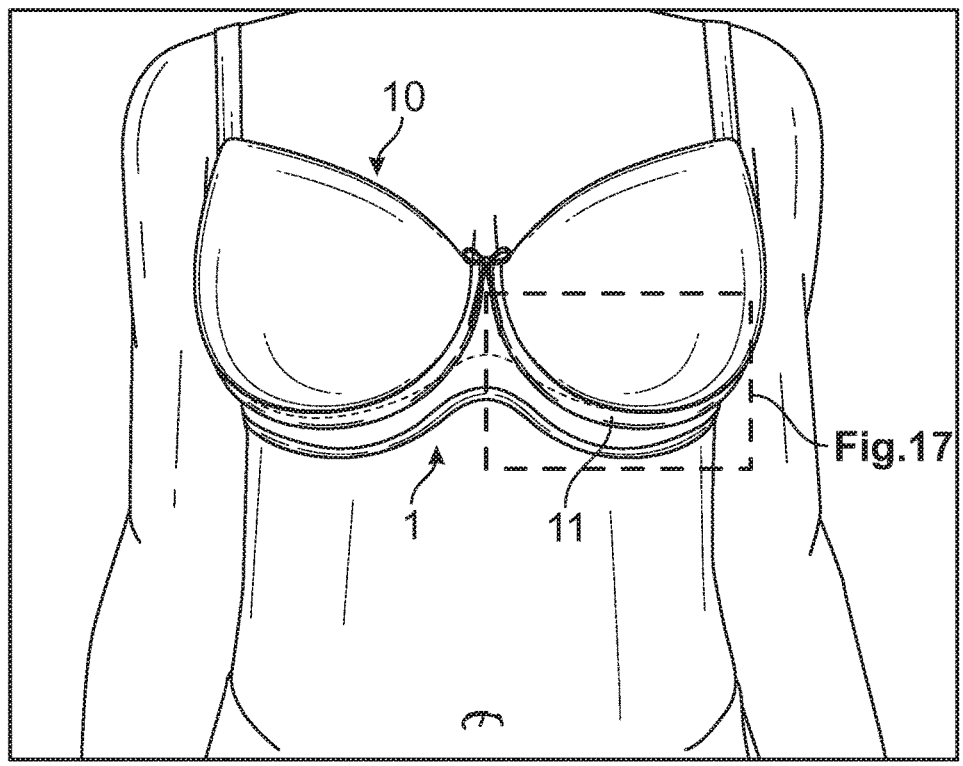
FIG. 16 illustrates a bra as source of pressure applied through a chest wall adapter device to the key sections of the inframammary fold, according to an embodiment.
Figure 17:
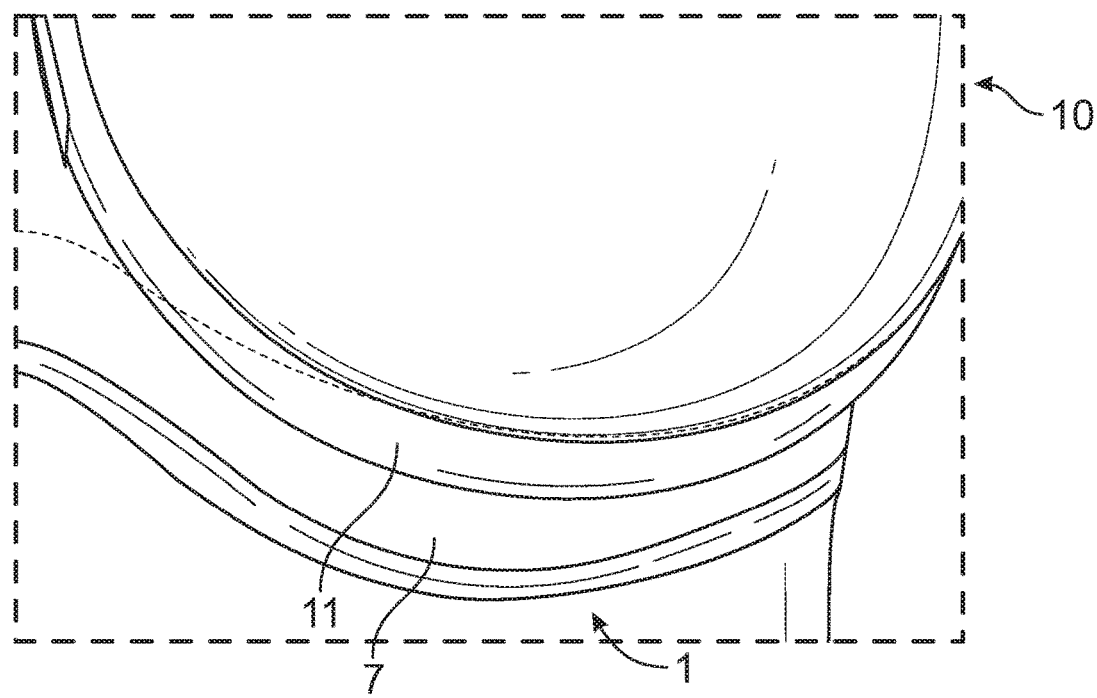
FIG. 17 illustrates an enlarged view of a portion of the bra and chest wall adapter device shown in FIG. 16, according to an embodiment.

FIGS. 16 and 17 show example arrangements in which the chest wall adapter device 1 is used in conjunction with a bra 10. In FIG. 16, a bra 10 functions as source of pressure applied through the chest wall adapter device 1 to the key sections of the inframammary fold of the breast, in an embodiment. FIG. 17 shows an enlarged view of a portion of the bra and chest wall adapter device shown in FIG. 16 (denoted by the broken-line box in FIG. 16). In an embodiment, the chest wall adapter device 1 is designed to be utilized in conjunction with a bra or other similar support mechanism to provide support to the user's breasts or breast implants. For example, the chest wall adapter device 1 may be customized (e.g., molded) to closely follow the contours of the user's chest wall, such that even if the uniform underwire of the bra bridges across any irregularities in the user's chest wall, the chest wall adapter device 1 continues to provide adequate pressure to the various regions of the inframammary fold of the breasts 6. The chest wall adapter device 1 allows the underwire 11 of the bra 10 to apply substantially uniform pressure across an irregularly-shaped chest, rather than apply an uneven amount of pressure at protruding points of the chest and/or no pressure at indentations of the chest. In an embodiment, the chest wall adapter device 1 may be anchored in place by a portion of a user's bra underwire 11 pressing firmly against the chest wall adapter device 1.

With reference to FIGS. 16 and 17, the underwire 11 of the bra 10 follows along the outward face or surface 7 of the chest wall adapter device 1 so that the outward face or surface 7 is between the underwire 11 and the user's skin, according to an embodiment. In such an embodiment, the chest wall adapter device 1 is contoured to fit the user's ribs and sternum and remains pressed against the user's chest by the bra 10. Because the chest wall adapter device 1 is molded to fit a particular area of the user's chest, it remains in that particular place when held by the underwire 11 of the bra 10. In one embodiment, the inner surface or face 5 of the downward-extending lip 3 of the chest wall adapter device 1 is lined with silicone or another malleable material for comfort. In an embodiment, the inner surface or face 5 of the downward-extending lip 3 is lined with silicone or another tacky material to prevent the breast support device 1 from slipping out of place.

The chest wall adapter device 1 may be created from a three-dimensional scan of the user's chest wall. In an embodiment, the chest wall adapter device 1 is designed to provide support to the user's breasts 6 or breast implants, regardless of any irregularities in the user's chest shape. For example, the chest wall adapter device 1 may be customized (e.g., molded) to closely follow the contours of the user's chest wall, such that the chest wall adapter device 1 does not bridge across any irregularities in the chest shape. In this manner, even when a user has one or more irregularities in their chest shape, the chest wall adapter device 1 continues to provide adequate support to the various regions of the inframammary fold of the breasts 6.

In some embodiments, the chest wall adapter device 1 is produced using an appropriate three-dimensional printing or other such additive manufacturing technique known in the art. For example, in an embodiment, the chest wall adapter device 1 is produced using digital rendering data from a three-dimensional rendering (e.g., generated from a three-dimensional scan) of the user's chest wall, or from another electronic data source (e.g., Additive Manufacturing File (AMF)). In some embodiments, data obtained or derived from upright MRI scans is used to produce the chest wall adapter device 1.

Figure 19:
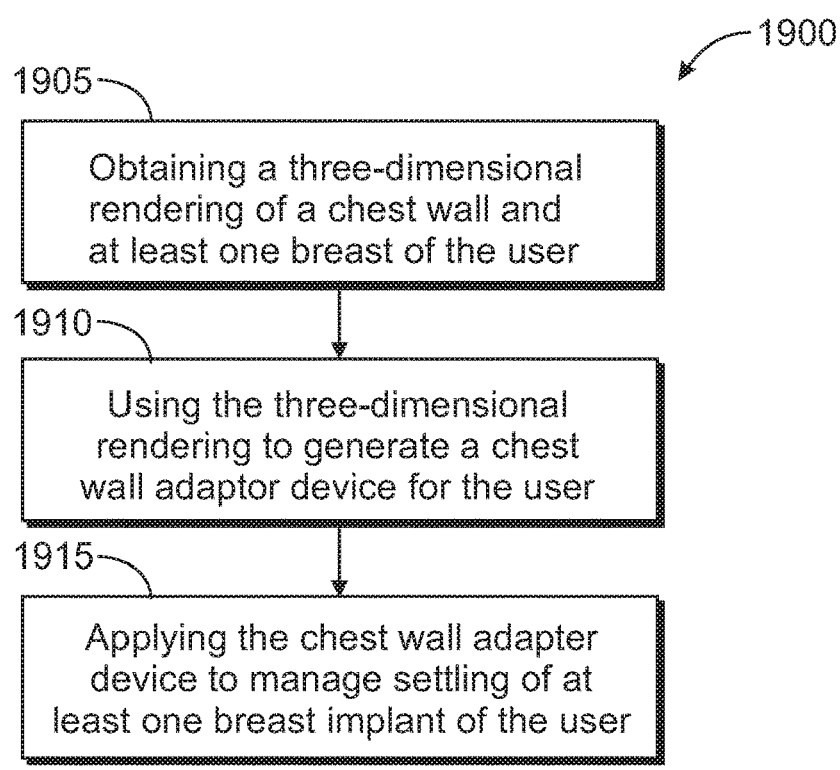
FIG. 19 is a flowchart illustrating an example process for managing settling of a breast implant, according to an embodiment.

FIG. 19 illustrates an example method 1900 for managing settling of a breast implant, according to some embodiments. In some embodiments, in addition to or instead of managing the settling of a breast implant, the method 1900 is for manipulating the shape of a user's breast (e.g., manipulating breast tissue regardless of whether or not a breast implant is involved). In at least one embodiment, the method of managing settling of a breast implant 1900 is designed to prevent undesirable settling of the breast implant following completion of breast augmentation or reconstruction surgery. For example, the method 1900 is implemented following submuscular breast implant surgery, according to an embodiment. In other embodiments, the method 1900 is implemented following one or more other types of breast surgery such as capsulorrhaphies to adjust the pocket. In some embodiments, the method 1900 is implemented before and/or after some other surgical or non-surgical procedure that involves or impacts the breast implants or breasts of the user. As discussed above, following submuscular breast implant surgery, a certain amount of settling of the breast implants is often desired, as the implants, if properly placed, are usually placed a little high on the patient's chest. For a period of time (e.g., one month to 6 months, etc.) following the surgery, the breast implants will settle downward until they have reached a level that is aesthetically pleasing to the patient (e.g., to give the desired "cleavage" or "fullness"). At that time, it is desirable to stop the settling process so that the breast implants maintain their current position and do not continue to drop downward beyond the point that is aesthetically pleasing to the patient. If nothing is done to arrest the settling process, the breast implants will continue to drop downward for a period of six to seven months following the surgery.

At block 1905, a three-dimensional rendering of a chest wall and at least one breast of the user is obtained. In some embodiments, the three-dimensional rendering of the chest wall and the at least one breast of the user obtained at block 1905 is a three-dimensional image of the chest wall and the at least one breast of the user. In some embodiments, the three-dimensional rendering of the chest wall and the at least one breast of the user obtained at block 1905 is a three-dimensional solid model drawing of the chest wall and the at least one breast of the user. Obtaining the three-dimensional rendering of the chest wall and the at least one breast of the user at block 1905 includes scanning the chest wall and the at least one breast of the user using a three-dimensional scanner, in an embodiment. In some embodiments, the three-dimensional rendering of the chest wall and the at least one breast of the user is obtained at block 1905 in response to determining whether a condition has been satisfied following completion of breast augmentation or reconstruction surgery. For example, in an embodiment, the three-dimensional rendering of the chest wall and the at least one breast of the user is obtained at block 1905 in response to determining that a threshold period of time has elapsed following the completion of breast augmentation or reconstruction surgery. This threshold period of time may be between five and seven weeks, in some embodiments. In other embodiments, this threshold period of time may be within several days (e.g., three days) before or after the date that falls six weeks following completion of breast augmentation or reconstruction surgery. In other embodiments, the threshold period of time is at least six weeks. In another example, the three-dimensional rendering of the chest wall and the at least one breast of the user is obtained at block 1905 in response to determining that a threshold amount of settling has occurred for the at least one breast implant of the user following completion of breast augmentation or reconstruction surgery. For example, the three-dimensional rendering of the chest wall and the at least one breast of the user may be obtained at block 1905 based on input received from the user that indicates a desirable amount of settling of the at least one breast implant has occurred, in an embodiment. Such input may include, for example, an indication that a desirable amount of settling has occurred and that no further settling is desired.

At block 1910, the three-dimensional rendering of the chest wall and the at least one breast of the user obtained at block 1905 is used to generate a chest wall adapter device for the user, in an embodiment. For example, the chest wall adapter device generated at block 1910 may be similar to the chest wall adapter device 1 discussed above and shown in detail in FIGS. 7-18, in some embodiments. Block 1910 may include using a three-dimensional printer to generate the chest wall adapter device based on digital rendering data associated with the three-dimensional rendering obtained at block 1905, in an embodiment.

At block 1915, the chest wall adapter device generated at block 1910 may be applied to manage the settling of at least one breast implant of the user, in an embodiment. In some embodiments, the chest wall adapter device generated at block 1910 is applied at block 1915 to manipulate a shape of the at least one breast of the user, whether or not the at least one breast includes a breast implant. In embodiments where at least one breast implant is involved, however, managing the settling of the at least one breast implant of the user at block 1915 may include a user wearing or utilizing the chest wall adapter device for a substantial portion (e.g., 80%, sixteen hours, etc.) of the day, for an extended period of time that comprises the course of treatment, in an embodiment. The extended period of time may be, for example, two months, six months, one year, etc., and may depend on the particular characteristics and anatomical particularities of the user. In some embodiments, the chest wall adapter device is worn during all waking hours of the day. In other embodiments, the chest wall adapter device is worn during at least fourteen hours in at least six days of each week during the extended period of time that comprises the course of treatment. In other embodiments, the chest wall adapter device is worn for a majority of all waking hours. In other embodiments, the chest wall adapter device is worn during all waking hours, except for no more than one hour a day for exercise, in which time a sports bra or other support mechanism is utilized. In yet other embodiments, the chest wall adapter device is worn by a user twenty-four hours a day, such as after capsulorrhaphy surgery.

Figure 12A:
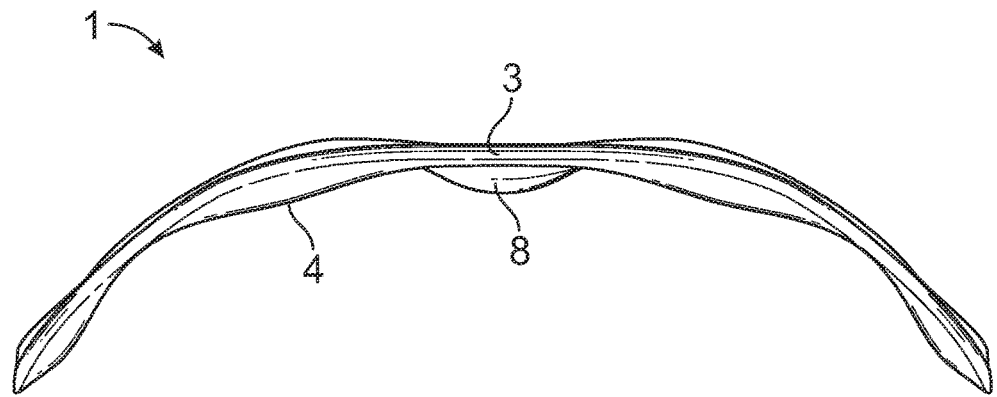
FIG. 12A illustrates a bottom view of the chest wall adapter device shown in FIG. 7, according to an embodiment.
Figure 12B:
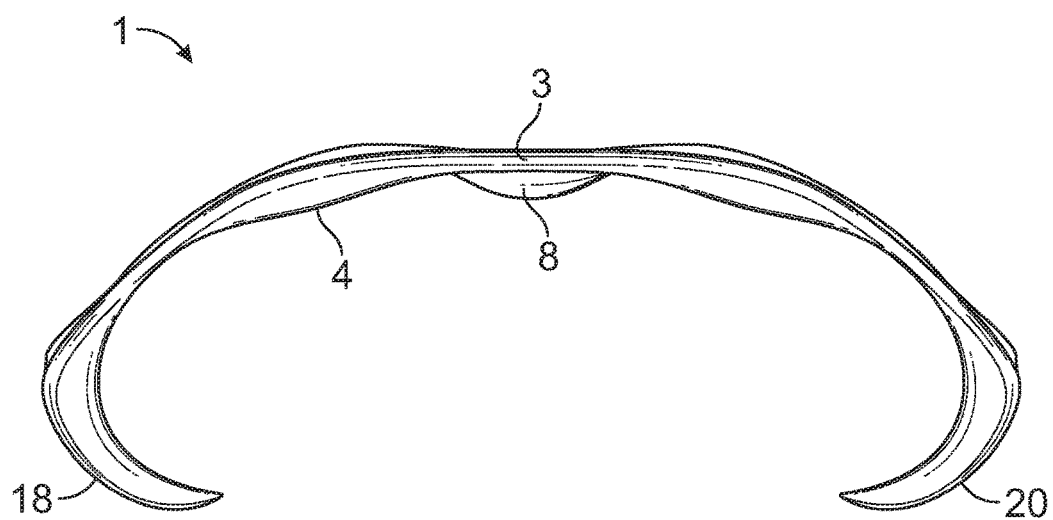
FIG. 12B illustrates a bottom view of an alternative embodiment of the chest wall adapter device shown in FIG. 12A, according to an embodiment.
Figure 13A:
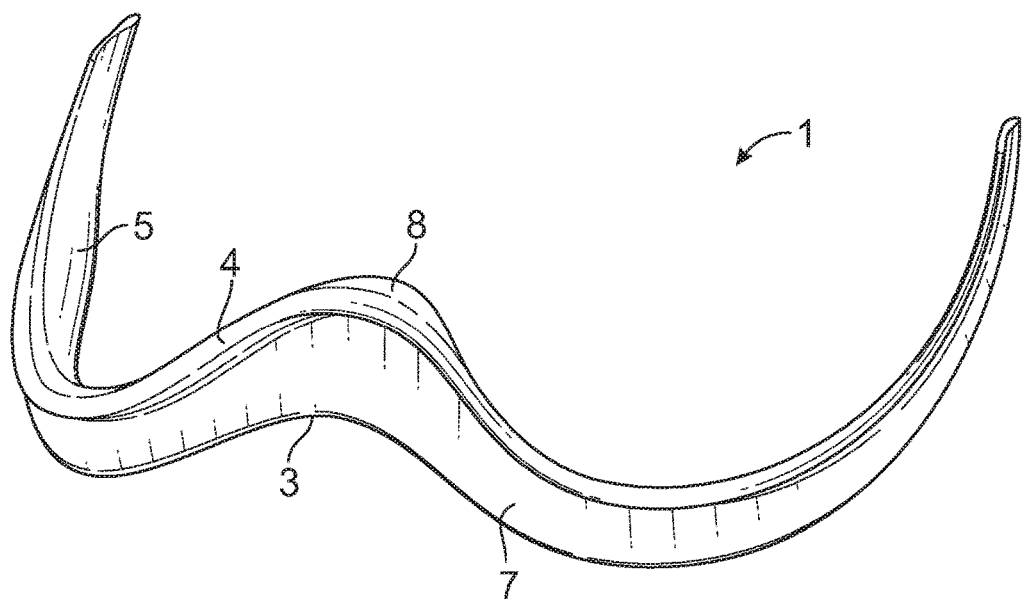
FIG. 13A illustrates a front perspective view of the chest wall adapter device shown in FIG. 7, according to an embodiment.
Figure 13B:
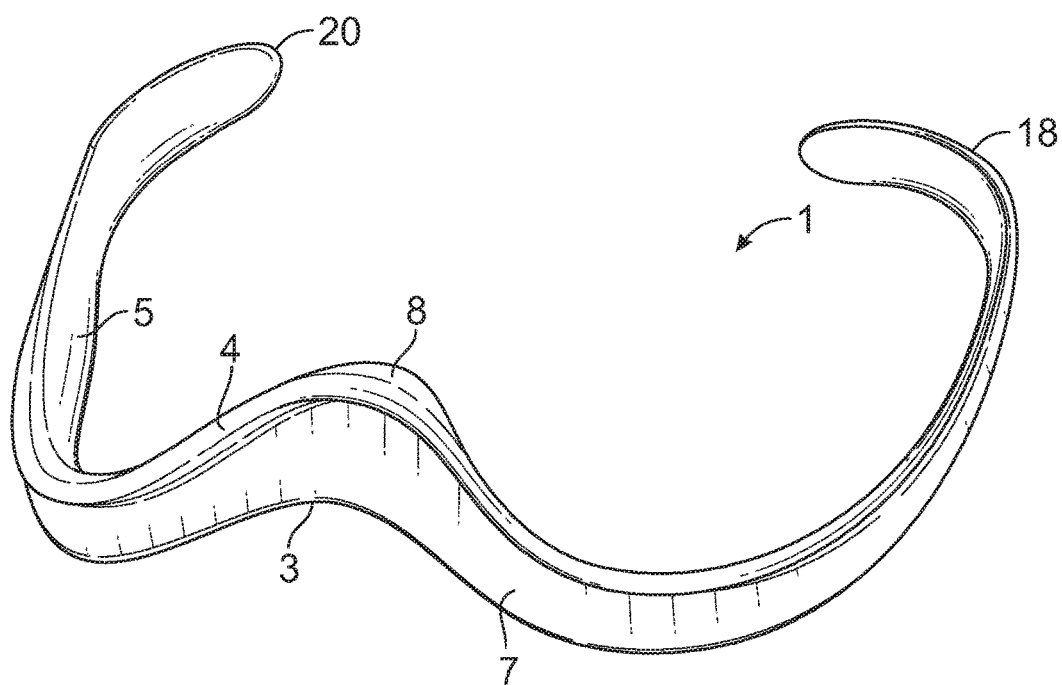
FIG. 13B illustrates a front perspective view of an alternative embodiment of the chest wall adapter device shown in FIG. 13A, according to an embodiment.

FIG. 12B and FIG. 13B illustrate an alternative embodiment of the chest wall adapter device 1, which includes a left thorax extension 18 and a right thorax extension 20. When the device 1 is worn by a user, the left thorax extension 18 wraps partially around the left side of the user's thorax while the right thorax extension 20 wraps partially around the right side of the user's thorax. The amount that the right and left thorax extensions wrap around may be variable, up to almost touching in the midline where there could be fixations. The thorax extensions 18 and 20 provide lateral stabilization.

In an embodiment, a chest wall adapter having a thorax extension provides the option of adding a cup that is interchangeable with other cups. With self-stabilization, there is the option of not needing a bra to supply a cup, however.

The device can be printed with an extension of the same material forming a cup or have interchangeable cloth (fabric or 3D printed) cups that attach to the device with, for example, Velcro®. The interchangeable cups can have their own straps.

An embodiment of the chest wall adapter device wraps around to the back of the wearer and makes the device potentially self-stabilizing. As such, the device can squeeze on the chest either in a front-back direction or right-left direction or both depending on how the printing is programmed.

With the extension to the back (printed off, for example, a 360 degree photo), unique force vectors can be created with programming far beyond the tightening of a noose action that a bra accomplishes. For example, tightening of a bra strap often does not increase pressure of the underwire at the areas of the meridian and sternal inframammary fold. But the extended version of the device printed in such a way that it "clamps" on the chest in a front-back manner will apply directed specific pressure to those areas of the inframammary fold. The extended version printed in such a way that it "clamps" on the chest more side-to-side will apply directed specific pressure to the sides of the chest stopping implant migration there which is a big problem in women that sleep on their stomachs, weightlift or have narrow sloped chests where the implants are on a ramp sloping to the side.

For certain chest wall shapes such as narrowing and sloping inward below the breasts and for certain breast sizes and shapes shoulder straps may be needed.

Printing the device with dimensions that provide transverse tightness helps to prevent the implants from falling to the side, such as may be the case for stomach sleepers weight lifters, patients with narrow chests, and patients having chests that are sloped acutely to the side.

Printing the device with dimensions that provide front-back tightness helps prevent downward setting of any implants in the first 7 months after pectus exavatum If a breast has sag [ptosis] then the lower breast is hidden in breast fold area from the 3D camera. For the various devices, sagging tissue should be lifted up for photography. Accordingly, in an embodiment, if a cup is to be provided and the breast has any sag then the breast should be taped for the scan so the 3D imager can pick up volume.

The chest wall adapter device (with or without the thorax extension) described herein has the potential to go beyond implant stabilization and into implant repositioning. Especially with elastic materials, such as nylon, the device can apply steady pressure to an implant to move it. An example is a woman whose implants are, early on after surgery, positioned too far to the side. The device (if printed narrow to push on the sides of the implant) can apply steady constant pressure up to 24 hours a day. Pushing toward the middle of the chest would likely be accompanied by printing a more narrow central portion of the device to allow room for the device to move to. In a similar fashion, a device could be printed to push an implant that is too low upward by raising the device on the side that is low. The device can further accomplish this pushing of the breasts together with a closed back, open front option that fastens in the front with a mechanism that allows the patient to gradually tighten the connection further. This is done by sliding one member of the 3D material over the other, so as to gradually narrow the connection. Another method is to gradually cut away advancing edges before binding them together.

In some embodiments, the time period of wear is measured from the surgery date, while in other embodiments, the period of wear is measured from when the implants have initially settled to the person's desired level. Once it is determined to stop the settling of the implants and one or more properly fit and position bras are obtained, they should be worn for an extended period. A chest wall adapter device as disclosed herein should be worn all day continuously while the person is awake and mobile. Most people do not need to wear the chest wall adapter device at night. It is acceptable to remove the chest wall adapter device for an hour or two while working out wearing a sports bra. In some embodiments, the chest wall adapter device can be worn underneath a sports bra. It is also acceptable to go to the beach and wear a bathing suit or bikini for a few hours. Nonetheless, other than these and similar exceptions, the chest wall adapter device should be worn continuously during waking hours until seven months after surgery, in some embodiments. In one embodiment, the chest wall adapter device is worn between six and seven months. After this extended period of wear time, it is optional for most people to wear the chest wall adapter device. It should be understood that there are some exceptions to the above with certain implant types, certain chest wall or rib shapes and certain procedures outside of standard sub muscular breast augmentation. Thus, while the period of six or seven months has been discussed previously, other periods of time may be appropriate for a particular person. For example, some people may only need to wear the chest wall adapter device for four or five months. Other people may require a longer period of wear time, such as eight or nine months.

For many individuals, during the first six months, the body is forming a normal lining around the implant called the capsule. The capsule does not reach its full strength until after this six month period. During that period, and occasionally afterwards, high resistance upper body exercise (i.e., weight-lifting, push-ups, pull-ups, etc.) will push the implant down and out. Users should be vigilant of the user's implant position especially if the user exercises during the first six months. The chest wall adapter device can help resist the downward and outward push on the implants from the pectoralis muscle. In one embodiment, the chest wall adapter device is used long-term to provide ongoing support and counterbalance to the pectoralis muscle.

Usually, a person is measured for the chest wall adapter device at least six weeks after surgery. If fitted before six weeks, there may be a fair amount of swelling, and so the chest wall adapter device may not fit properly later on. There are occasional people who are happy with implant levels before six weeks. In such instances, the person may wear any underwire bra they want, or even a sports bra, as long as the underwire does not irritate the scar in the fold area. However, it is unlikely that a chest wall adapter device that is properly sized and fit to a person before the six weeks will be acceptable for the later extended wear period. In such situations, a second or additional chest wall adapter device can be created to achieve proper support as the inflammation subsides.

After six months, there may also be a concern about implants falling to the side, even years after surgery. The most important factors that contribute to implants falling to the side are sleeping on one's stomach, chest shape (where the breast bone is more projecting) leaving the implant platform on a slope, prominent ribs on one side, and weight lifting. After the first six months, if a woman notices that her implants fall to the side, it is worth intervening in this trend. Wearing a chest wall adapter device at night that is comfortable and supports the implants from the sides can help slow or stop the process. In such an embodiment, the chest wall adapter device may have a higher or extended side supports that push the breasts inward toward the center.

It should be noted that the chest wall adapter device of present disclosure may be used in connection with various other forms of breast surgery in addition to or instead of breast augmentation surgery. For example, the chest wall adapter device may provide numerous benefits to a user following reconstructive breast surgery, breast reduction surgery, or any other procedure which leaves one or both breasts in need of support. It should also be understood that the chest wall adapter device described herein is designed for use by any gender, and is not limited in its application to breasts of any particular size and/or shape. It can be applied after fat grafting to the breast to control fat graft migration.

Turning to FIGS. 20A-20D, a chest wall adapter apparatus (the "device") according to another embodiment will now be described. In this embodiment, the device stabilized with an upper breast prong that obviates the need for any overlying source of pressure (such as bra). The device, generally labeled 2000, is a unibody piece that has a right section 2001a and a left section 2001b and that wraps partially around a user from a closed front side 2002a to an open rear side 2002b. In other words, the right section 2001a and the left section 2001b are contiguous in the front side 2002a, whereas in the rear side 2002b, there is a gap between the two sections. The device 2000 has a right thorax extension 2003a that ends at a terminus 2004a, a left thorax extension 2003b that ends at a left terminus 2004b, and a central portion 2006. Each of the right and left thorax extensions 2003a and 2003b wrap at least partially around the user's thorax. In the embodiment of FIGS. 20A-20D, there is a gap between the right terminus 2004a and the left terminus 2004b. In an embodiment, in order to adjust the width of the gap, the device 2000 includes a mechanism for closing the gap (e.g., joining the right and left thorax extensions 2003a and 2003b together). Examples of suitable mechanisms include: a connector such as a strap (e.g., Velcro®) and a tongue and groove joint.

Referring still to FIGS. 20A-20D, the device 2000 also includes a right stabilization prong 2008a that extents upwardly from the right section 2001a and a left stabilization prong 2008b that extents upwardly from the left section 2001b. When the device 2000 is worn by a user, the right stabilization prong 2008a wraps around an outer portion of the right breast of the user and ends in a taper 2010a on the top of the right breast. Similarly, the left stabilization prong 2008b wraps around an outer portion of the left breast of the user and ends in a taper 2010b on the top of the left breast. The device 2000 further includes a horizontally extending and upwardly angled right shelf 2012a that extends from the central portion 2006 to the right stabilization prong 2008a and that defines a curved edge corresponding to an inframammary fold of the right breast of the user, and, similar to the embodiments of FIGS. 7-20, a horizontally extending and upwardly angled left shelf 2012b that extends from the central portion 2006 to the left stabilization prong 2008b and that defines a curved edge corresponding to an inframammary fold of the right breast of the user. The device 2000 further includes an adapter wall 2014 that extends from the right stabilization prong 2008a to the left stabilization prong 2008b. The central portion 2006 is part of the adapter wall 2014. The adapter wall 2014 is integrally formed with the right shelf 2012a and the left shelf 2012b and extends in a direction perpendicular or substantially perpendicular to the left and right shelves 2012a and 2012b. The adapter wall has an outer face 2014a and an inner face 2014b. The inner face has an inwardly extending convex portion 2015 located between the right section 2001a and the left section 2001b. The convex portion 2015 is configured to lie against the chest wall of the user between the breasts.

The intersection of the right shelf 2012a and the adapter wall 2014 forms a first curve 2016a whose shape corresponds to a contour on the inframammary fold of the right breast of the user (e.g., as measured by the physician in preparation for 3D printing the device). Similarly, the intersection of the left shelf 2012b and the adapter wall 2014 forms a second curve 2016b whose shape corresponds to a contour on the inframammary fold of the left breast of the user.

In an embodiment, the device 2000 further includes a tab 2018 that extends from the central portion 2006. The tab 2018 sits against the user's sternum and provides additional support to the left and right breasts of the user. In the embodiment depicted in FIGS. 20A-20D, the tab 2018 includes a right prong 2020a that sits against the right breast when the device 2000 is worn and a left prong 2020b that sits against the left breast when the device 2000 is worn. The right and left prongs 2020a and 2020b are joined by a concave cutout 2022.

Figure 20A:
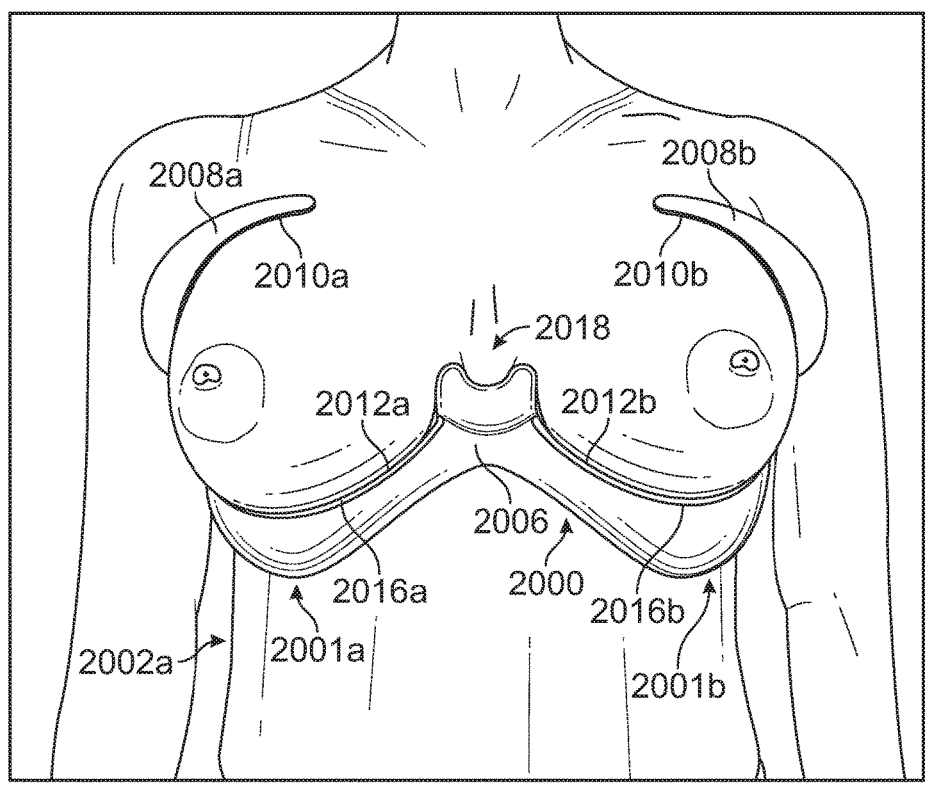
FIG. 20A illustrates a front view of a chest wall adapter (while worn) according to another embodiment.
Figure 20B:
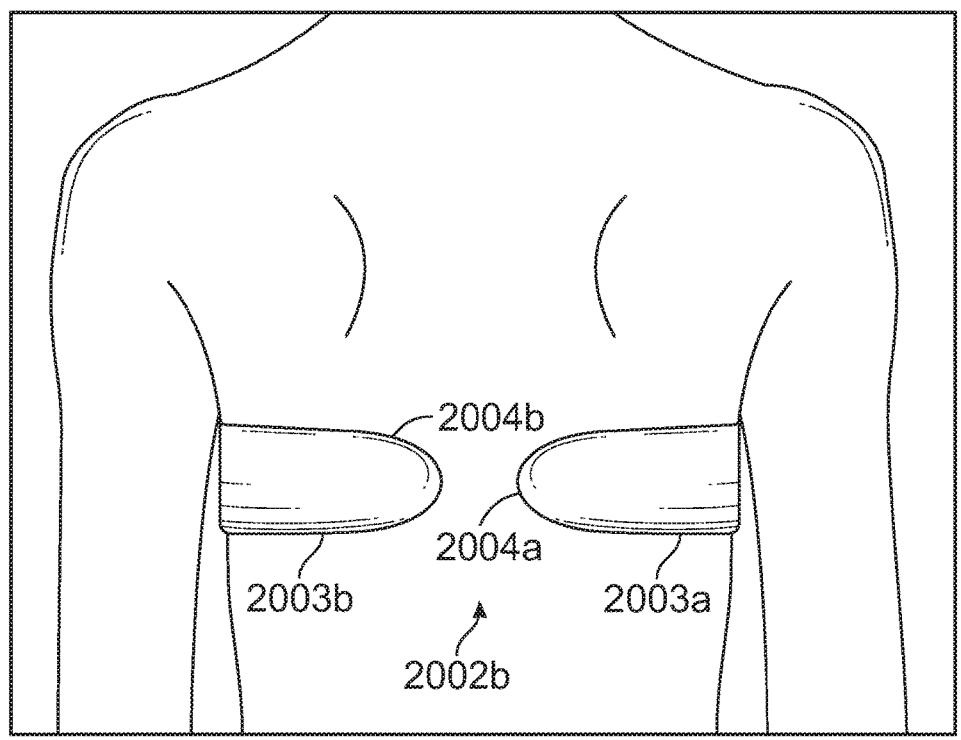
FIG. 20B illustrates a rear view of the chest wall adapter of FIG. 20A.
Figure 20C:
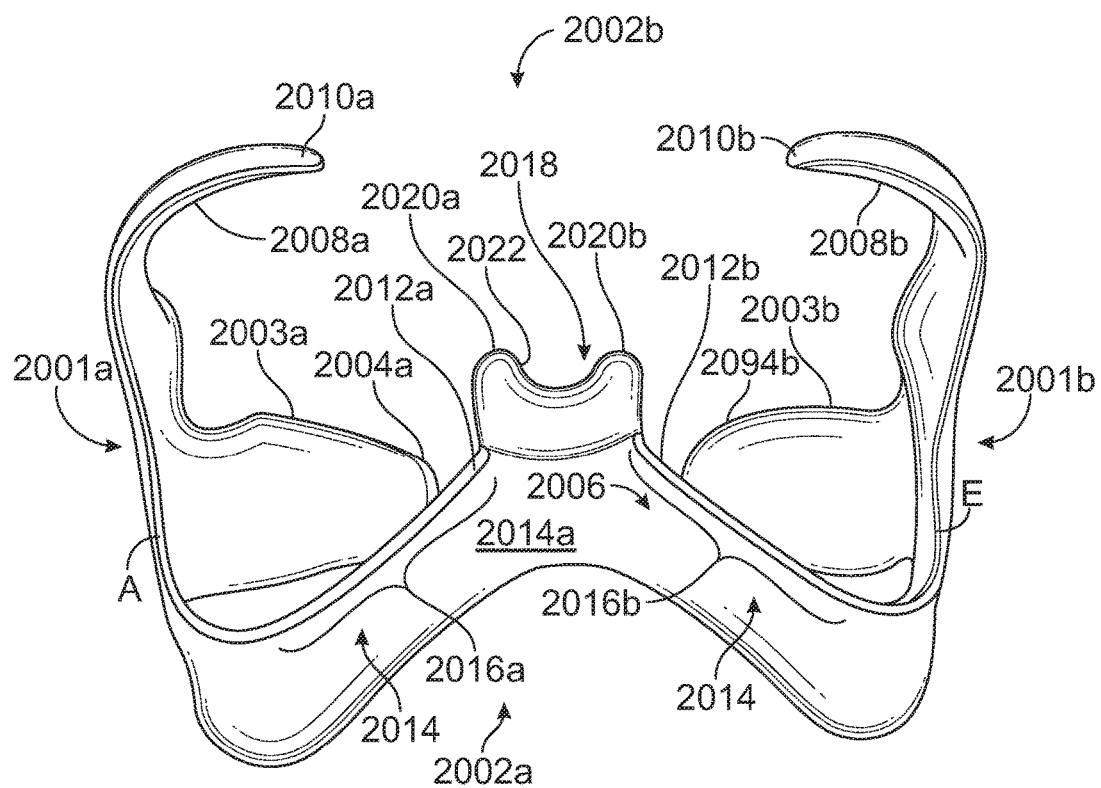
FIG. 20C illustrates a front view of the chest wall adapter of FIG. 20A while not being worn.
Figure 20D:
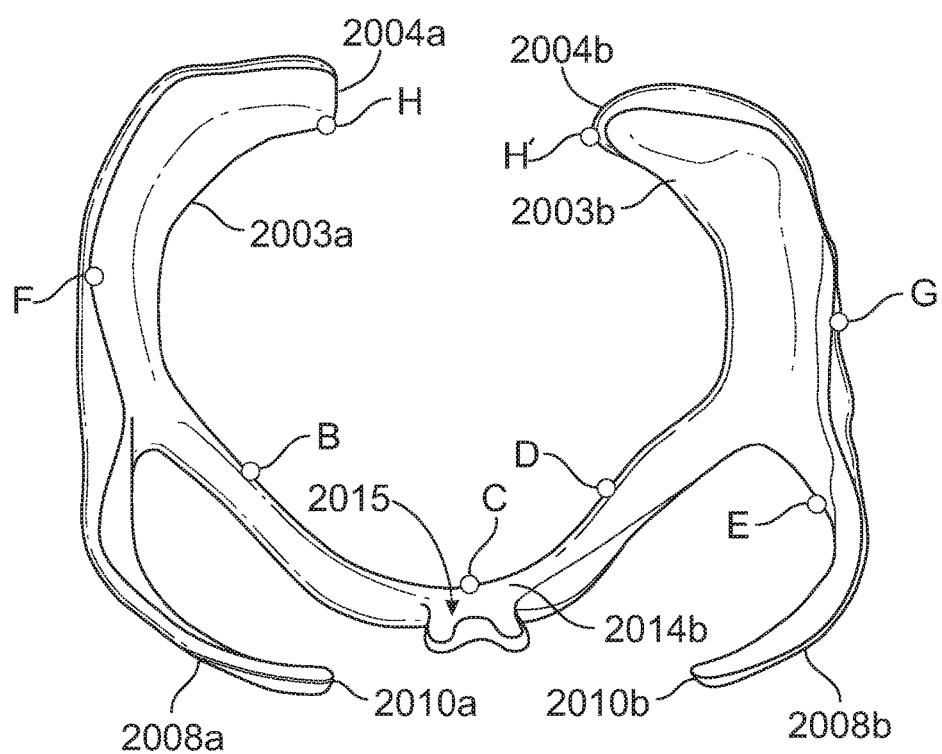
FIG. 20D illustrates a top view of the chest wall adapter of FIG. 20A while not being worn.
Figure 21A:
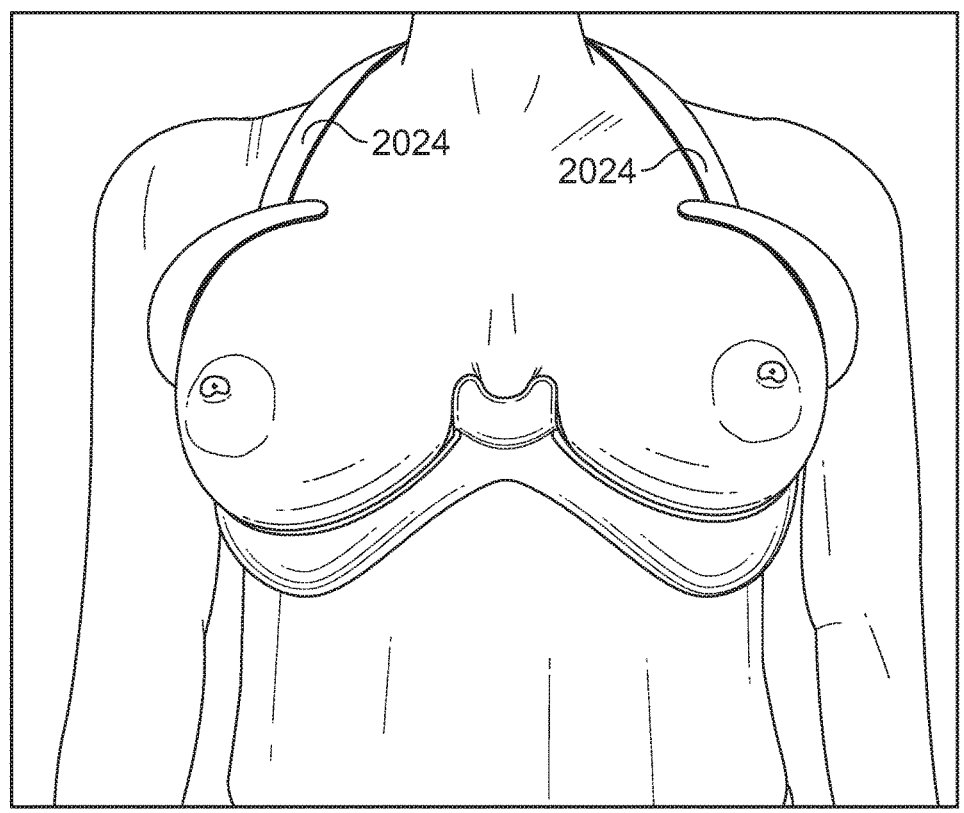
FIG. 21A illustrates a front view of a variation of the chest wall adapter of FIG. 20A.
Figure 21B:
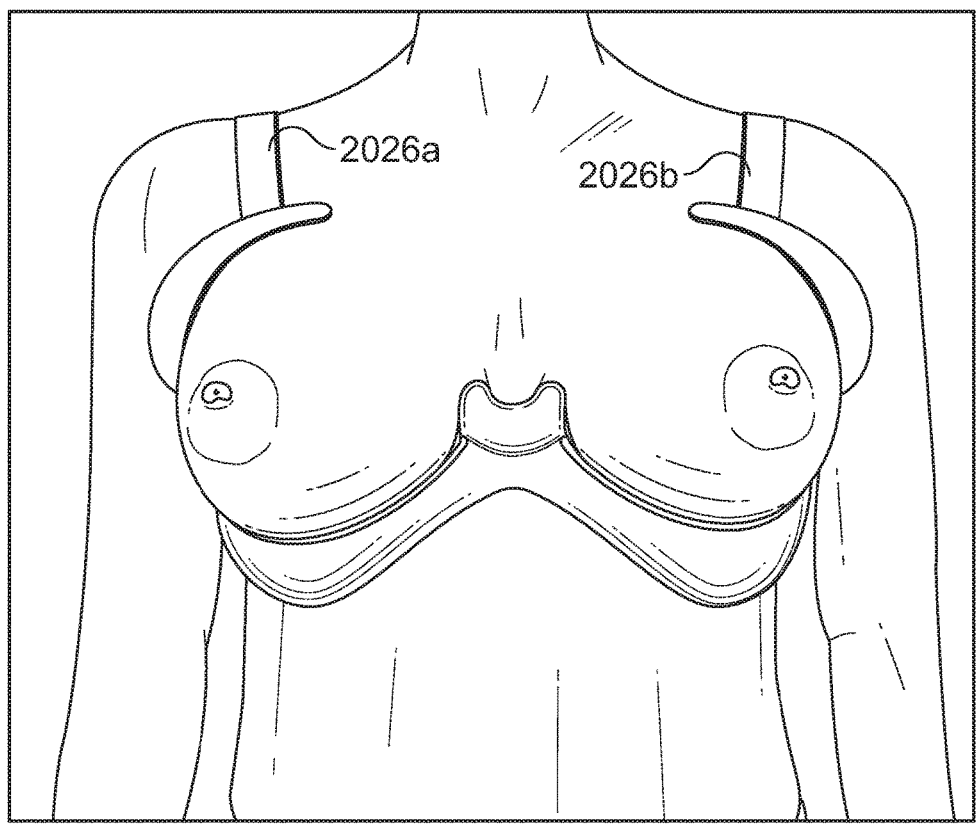
FIG. 21B illustrates a front view of another variation of the chest wall adapter of FIG. 20A.
Figure 21C:
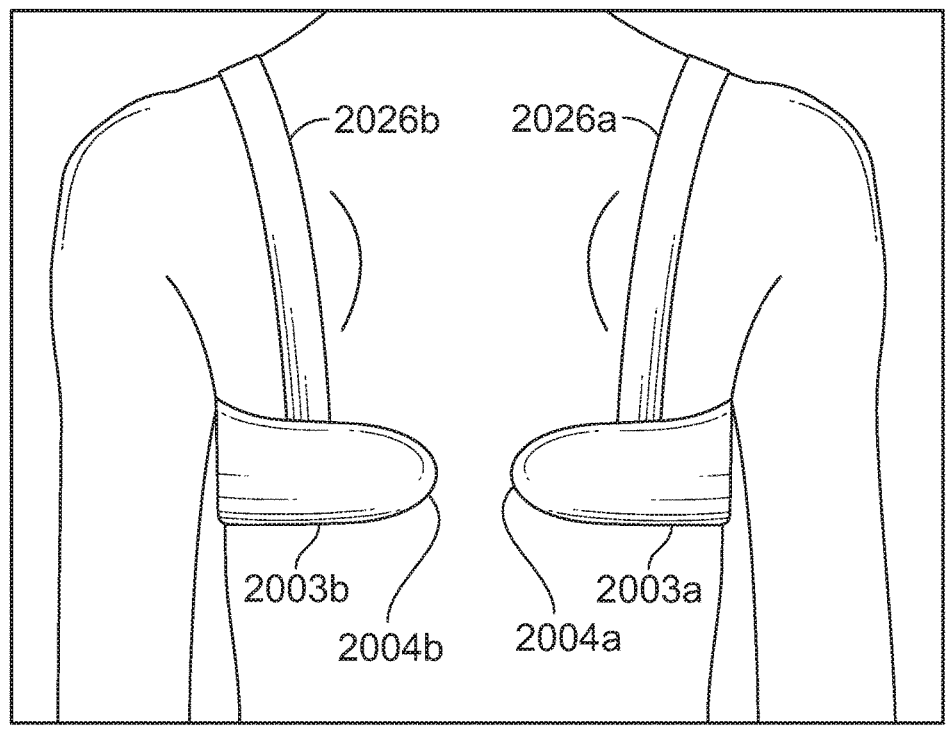
FIG. 21C illustrates a rear view of the chest wall adapter of FIG. 21B.

FIGS. 20C and 20D show certain landmarks for constructing (e.g., 3D printing) the device to carry out chest squeeze (clamping) and for breast and/or breast implant manipulation. For example, configuring the 3D data to print the device such that points F and G (FIG. 20D) are closer together further prevents implants from falling to the side which tends to occur with patients who are, stomach sleepers, weight lifters, have narrow chests, and have chests sloped acutely to the side. Configuring the 3D data H and H' closer to B and D (FIG. 20D) puts more pressure at the 3 sites along the inframammary fold needed to stop implants from migrating downward and keeps implants from migrating together over the breast bone in cases of pectus excavatum In various embodiments, the device 2000 (from FIGS. 20A-20D) includes one or more straps. For example, in the embodiment depicted in FIG. 21A, the device 2000 includes a halter strap 2024 attached to both the right stabilization prong 2008a and the left stabilization prong 2008b. In the embodiment depicted in FIG. 21B and FIG. 21C, the device 2000 includes a right strap 2026a attached at one end to the left stabilization prong 2008a and attached at the other end to the right thorax extension 2003a, and a left strap 2026b attached to the right stabilization prong 2008b at one and to the left thorax extension 2003b at the other end.

Figure 22A:
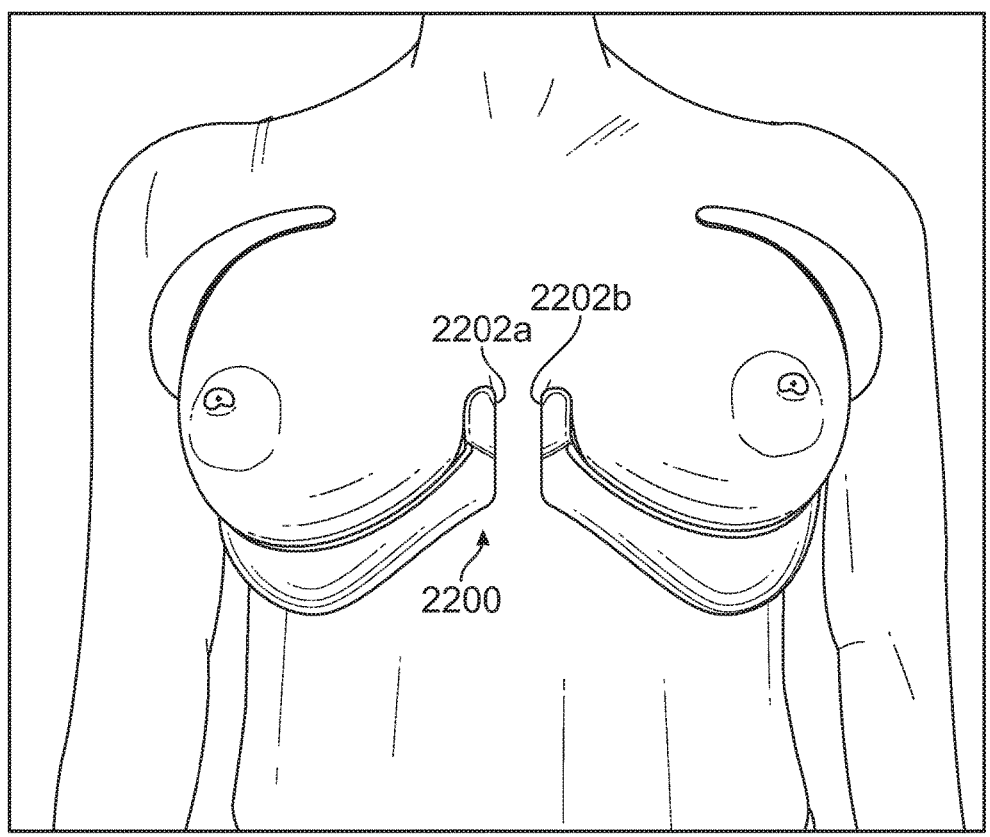
FIG. 22A depicts a front view of an open front, closed back embodiment of the device of FIG. 20A.
Figure 22B:
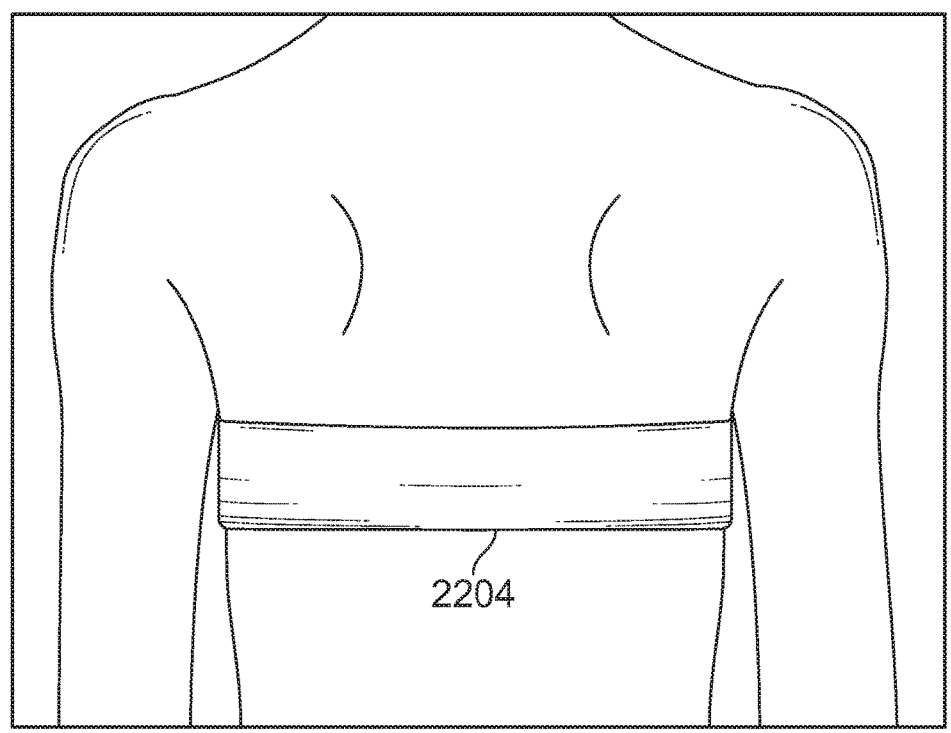
FIG. 22B is a rear view of the device of FIG. 22A.
Figure 22C:
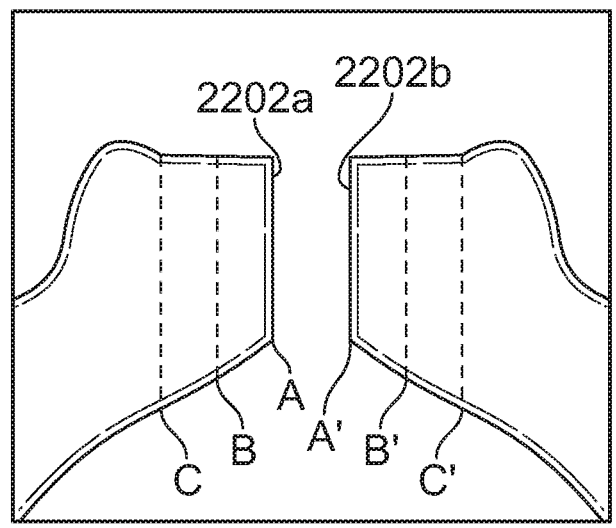
FIG. 22C is a close up view of a front opening of a variation of the device of FIG. 22A.
Figure 22D:
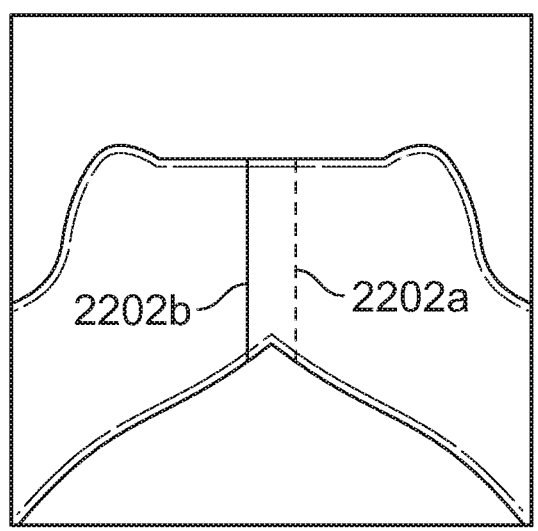
FIG. 22D is a close up view of a front opening of another variation of the device of FIG. 22A.

According to an embodiment, a variation of the device 2000 of FIGS. 20A-20D is open in the front and closed in the back. Turning to FIG. 22A and FIG. 22B, in this variation, the device (generally labeled 2200) on the front side 2002a, the tab 2018 is split between first edge 2202a and a second edge 2202b, which bound a gap. On the rear side 2002b, instead of the two thorax extensions, there is a single piece 2204 that joins the two halves of the device 2200. In order to adjust the width of the device 2200 in an embodiment, the front opening portion is provided with excess material that may be cut away prior to joining the two halves, as depicted in FIG. 22C. For example, cuts can be made at lines B and B' or at lines C and C', after which the halves are joined. In other embodiments, a joining mechanism such as a strap (e.g., Velcro®) or a tongue and groove joint may be provided. FIG. 22D shows the two halves drawn together in which the two edges 2202a and 2202b are overlapped with one another (by a variable amount), thereby drawing the breasts together. The configuration of FIG. 22D would work well, for example, if the material at the front opening was made of nylon.

It will be apparent to one of skill in the art how alternative functional configurations can be implemented to implement the desired features of the present disclosure. Additionally, with regard to flow diagrams, operational descriptions and method claims, the order in which the steps are presented herein shall not mandate that various embodiments be implemented to perform the recited functionality in the same order unless the context dictates otherwise.

All references, including publications, patent applications, and patents, cited herein are hereby incorporated by reference to the same extent as if each reference were individually and specifically indicated to be incorporated by reference and were set forth in its entirety herein.

For the purposes of promoting an understanding of the principles of the disclosure, reference has been made to the embodiments illustrated in the drawings, and specific language has been used to describe these embodiments. However, no limitation of the scope of the disclosure is intended by this specific language, and the disclosure should be construed to encompass all embodiments that would normally occur to one of ordinary skill in the art. Descriptions of features or aspects within each embodiment should typically be considered as available for other similar features or aspects in other embodiments unless stated otherwise. The terminology used herein is for the purpose of describing the particular embodiments and is not intended to be limiting of exemplary embodiments of the disclosure. In the description of the embodiments, certain detailed explanations of related art are omitted when it is deemed that they may unnecessarily obscure the essence of the disclosure.

The use of any and all examples, or exemplary language (e.g., "such as") provided herein, is intended merely to better illuminate the disclosure and does not pose a limitation on the scope of the disclosure. Numerous modifications and adaptations will be readily apparent to those of ordinary skill in this art without departing from the scope of the disclosure. Therefore, the scope of the disclosure is defined not by the detailed description of the disclosure, and all differences within the scope will be construed as being included in the disclosure.

No item or component is essential to the practice of the disclosure unless the element is specifically described as "essential" or "critical". It will also be recognized that the terms "comprises," "comprising," "includes," "including," "has," and "having," as used herein, are specifically intended to be read as open-ended terms of art. The use of the terms "a" and "an" and "the" and similar referents in the context of describing the disclosure are to be construed to cover both the singular and the plural, unless the context clearly indicates otherwise. In addition, it should be understood that although the terms "first," "second," etc. may be used herein to describe various elements, these elements should not be limited by these terms, which are only used to distinguish one element from another.

Furthermore, recitation of ranges of values herein are merely intended to serve as a shorthand method of referring individually to each separate value falling within the range, unless otherwise indicated herein, and each separate value is incorporated into the specification as if it were individually recited herein.

What is claimed is:

1. A chest wall adapter apparatus for supporting a user's breasts, the apparatus comprising:
   a right section;
   a left section,
   wherein the right section and the left section are contiguous on a front side of the apparatus;
   an inwardly extending convex portion located between the right section and the left section, wherein the inwardly extending convex portion is configured to lie against the chest wall of the user between the breasts;
   a horizontally extending and upwardly angled right shelf configured to extend along the right section and follow a contour along an underside of a right breast of the user;
   a horizontally extending and upwardly angled left shelf configured to extend along the left section and follow a contour along an underside of the left breast of the user;
   a vertically extending adapter wall, having an inner face and an outer face, a top of the vertically extending adapter wall is integrally formed with the shelf and defines a curved edge corresponding to an inframammary fold of the breasts of the user, the inner face is configured to lie against the user's chest wall beneath the breasts of the user;
   a right thorax extension that extends from the right section on a rear side of the apparatus so as to wrap at least partially around a thorax of the user; and
   a left thorax extension that extends from the left section on a rear side of the apparatus so as to wrap at least partially around a thorax of the user.

2. The apparatus of claim 1, wherein the convex portion is alternatively formed as a concave portion having a shape corresponding to a prominence in the chest wall of the user.

3. The apparatus of claim 1, wherein the shelf has a width varying between a center point of the apparatus and a lateral end of the apparatus.

4. The apparatus of claim 1, wherein the shelf has a width gradually decreasing as the shelf extends laterally outward from a center point of the apparatus.

5. The apparatus of claim 1, wherein the shelf has a width in a range of 0.5 to 2.0 inches.

6. The apparatus of claim 1, wherein the adapter wall extends 1.0 to 2.0 or less inches from the point of intersection with the shelf.

7. A chest wall adapter apparatus for supporting a user's breasts, the apparatus comprising:
   a right section;
   a left section,
   wherein the right section and the left section are contiguous on a front side of the apparatus;
   a horizontally extending and upwardly angled shelf configured to extend along the left section and the right section and follow a contour along at least an underside of the breasts of the user;
   a vertically extending adapter wall, having an inner face and an outer face,
   wherein a top of the vertically extending adapter wall is integrally formed with the shelf and defines a curved edge corresponding to an inframammary fold of the breasts of the user, the inner face is configured to lie against the user's chest wall beneath the breasts of the user;
   a right stabilization prong that extends upwardly from the right section so as to wrap at least partially around a top of a right breast of the user; and
   a left stabilization prong that extends upwardly from the left section so as to wrap at least partially around a top of a left breast of the user.

8. The apparatus of claim 7, further comprising an inwardly extending convex portion located between the first end of the left section and the first end of the right section, wherein the inwardly extending convex portion is configured to lie against the chest wall of the user between the breasts.

9. The apparatus of claim 7, further comprising:
   a right thorax extension that extends from the right section on a rear side of the apparatus so as to wrap at least partially around a thorax of the user; and
   a left thorax extension that extends from the left section on a rear side of the apparatus so as to wrap at least partially around a thorax of the user.

10. The apparatus of claim 9, further comprising a first strap having a first end and a second end and a second strap having a first end and a second end,
   wherein the first strap that is attached to the right stabilization prong at its first end and is attached to the right thorax extension at the second end,
   wherein the second strap that is attached to the left stabilization prong at its first end and is attached to the left thorax extension at its second end.

11. The apparatus of claim 9, wherein each of the right thorax extension and the left thorax extension includes a clamping mechanism for joining the right thorax extension and the left thorax extension.

12. The apparatus of claim 7, further comprising a strap having a first end and a second end, wherein the strap that is attached to the right stabilization prong at the first end and is attached to the left stabilization prong at the second end.

13. The apparatus of claim 7, further comprising at least one bra cup that is attachable to the right section or the left section.

14. A chest wall adapter apparatus for supporting a user's breasts, the apparatus comprising:
   a right section;
   a left section,
   wherein the right section and the left section are contiguous on a rear side of the apparatus via a back supporting piece, wherein the right section and the left section a separated by a gap on a front side of the apparatus;

a horizontally extending and upwardly angled shelf configured to extend along the left section and the right section and follow a contour along at least an underside of the breasts of the user;

a vertically extending adapter wall, having an inner face and an outer face, a top of the vertically extending adapter wall is integrally formed with the shelf and defines a curved edge corresponding to an inframammary fold of the breasts of the user, the inner face is configured to lie against the user's chest wall beneath the breasts of the user;

a left stabilization prong that extends upwardly from the left section so as to wrap at least partially around a top of a left breast of the user when worn; and a right stabilization prong that extends upwardly from the right section so as to wrap at least partially around a top of a right breast of the user when worn.

15. The apparatus of claim 14, further comprising a first strap having a first end and a second end and a second strap having a first end and a second end, wherein the first strap that is attached to the right stabilization prong at its first end and is attached to the back supporting piece at its second end, wherein the second strap that is attached to the left stabilization prong at its first end and is attached to the back supporting piece at its second end.

16. The apparatus of claim 14, further comprising a strap having a first end and a second end, wherein the strap that is attached to the right stabilization prong at the first end and is attached to the left stabilization prong at the second end.

17. The apparatus of claim 14, further comprising at least one bra cup that is attachable to either the right section or the left section.

18. The apparatus of claim 14, further comprising a mechanism for closing the gap to join the right section and the left section.

19. The apparatus of claim 18, wherein the mechanism comprises excess material that may be cut off from edges that bound the gap.

20. The apparatus of claim 18, wherein the mechanism is a clamping mechanism to allow edges that bound the gap to be drawn together so as to overlap a variable amount.

* * * * *